US012048801B2

(12) United States Patent
Bartels et al.

(10) Patent No.: US 12,048,801 B2
(45) Date of Patent: Jul. 30, 2024

(54) AEROSOL DELIVERY OF PIRFENIDONE

(71) Applicant: SOFTHALE NV, Diepenbeek (BE)

(72) Inventors: Frank Bartels, Hattingen (DE); Jürgen Rawert, Cologne (DE)

(73) Assignee: INVOX BELGIUM NV, Diepenbeek (BE)

( * ) Notice: Subject to any disclaimer, the term of this patent is extended or adjusted under 35 U.S.C. 154(b) by 935 days.

(21) Appl. No.: 16/624,224

(22) PCT Filed: Jun. 22, 2018

(86) PCT No.: PCT/EP2018/066719
§ 371 (c)(1),
(2) Date: Dec. 18, 2019

(87) PCT Pub. No.: WO2018/234527
PCT Pub. Date: Dec. 27, 2018

(65) Prior Publication Data
US 2021/0146065 A1    May 20, 2021

Related U.S. Application Data

(60) Provisional application No. 62/523,581, filed on Jun. 22, 2017.

(30) Foreign Application Priority Data

Jun. 22, 2017   (EP) ...................................... 17177459

(51) Int. Cl.
*A61M 11/00*     (2006.01)
*A61K 9/00*      (2006.01)
(Continued)

(52) U.S. Cl.
CPC ........... *A61M 11/007* (2014.02); *A61K 9/008* (2013.01); *A61K 31/4412* (2013.01); *A61M 11/002* (2014.02); *A61M 15/00* (2013.01)

(58) Field of Classification Search
CPC .. A61M 11/00; A61M 11/002; A61M 11/007; A61M 11/008; A61M 15/00;
(Continued)

(56) References Cited

U.S. PATENT DOCUMENTS 2,235,258 A * 3/1941 Jones ........................ B05B 1/14
169/37
5,497,944 A * 3/1996 Weston ................. B05B 11/026
128/200.22
(Continued)

FOREIGN PATENT DOCUMENTS

| CN | 1950121 A | 4/2007 |
|---|---|---|
| EP | 0 627 230 | 2/2000 |
| WO | WO 2014/018668 | 1/2014 |

*Primary Examiner* — Justine R Yu
*Assistant Examiner* — Matthew R Moon
(74) *Attorney, Agent, or Firm* — HOXIE & ASSOCIATES LLC

(57) ABSTRACT

The invention relates to the field of inhalation methods and inhalation devices for liquids. In particular, the invention relates to an inhalation method using an inhalation device having a nebulizing nozzle, and to a method for the generation of an aerosol of an aqueous formulation comprising pirfenidone by means of such inhalation device.

23 Claims, 6 Drawing Sheets

(51) Int. Cl.
*A61K 31/4412* (2006.01)
*A61M 15/00* (2006.01)

(58) Field of Classification Search
CPC .......... A61M 2206/16; A61M 15/0003; A61K 9/0073; A61K 9/008; A61K 31/4412; A61P 11/00
See application file for complete search history.

(56) References Cited

U.S. PATENT DOCUMENTS

| | | |
|---|---|---|
| 5,911,851 A | 6/1999 | Bartels et al. |
| 5,964,416 A | 10/1999 | Jaeger et al. |
| 8,313,717 B2 | 11/2012 | Boe |
| 9,259,540 B2 | 2/2016 | Dunne |
| 9,517,204 B2 | 12/2016 | Onoue et al. |
| 10,092,552 B2 | 10/2018 | Surber |
| 10,105,501 B2 | 10/2018 | Giroux et al. |
| 2005/0263618 A1 | 12/2005 | Spallek et al. |
| 2013/0130192 A1 | 5/2013 | Schmitt |
| 2014/0251320 A1* | 9/2014 | Giroux .................. B05B 7/0869 128/200.21 |

* cited by examiner

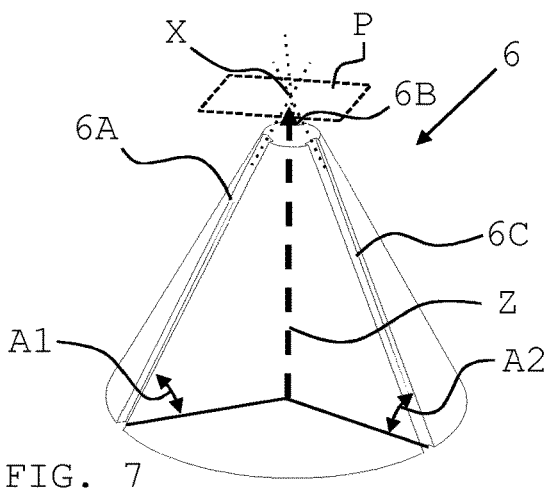
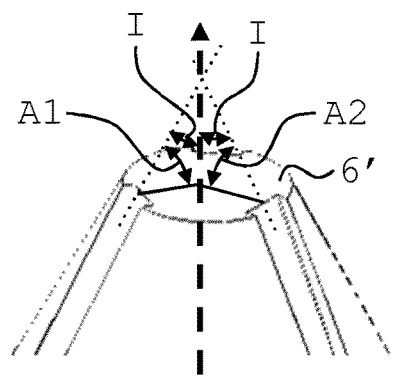
FIG. 7
FIG. 8
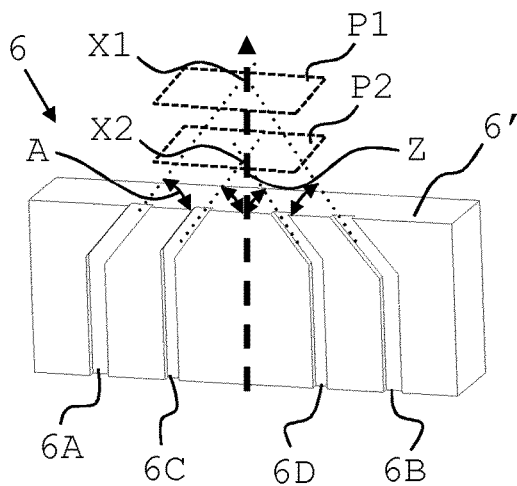
FIG. 9
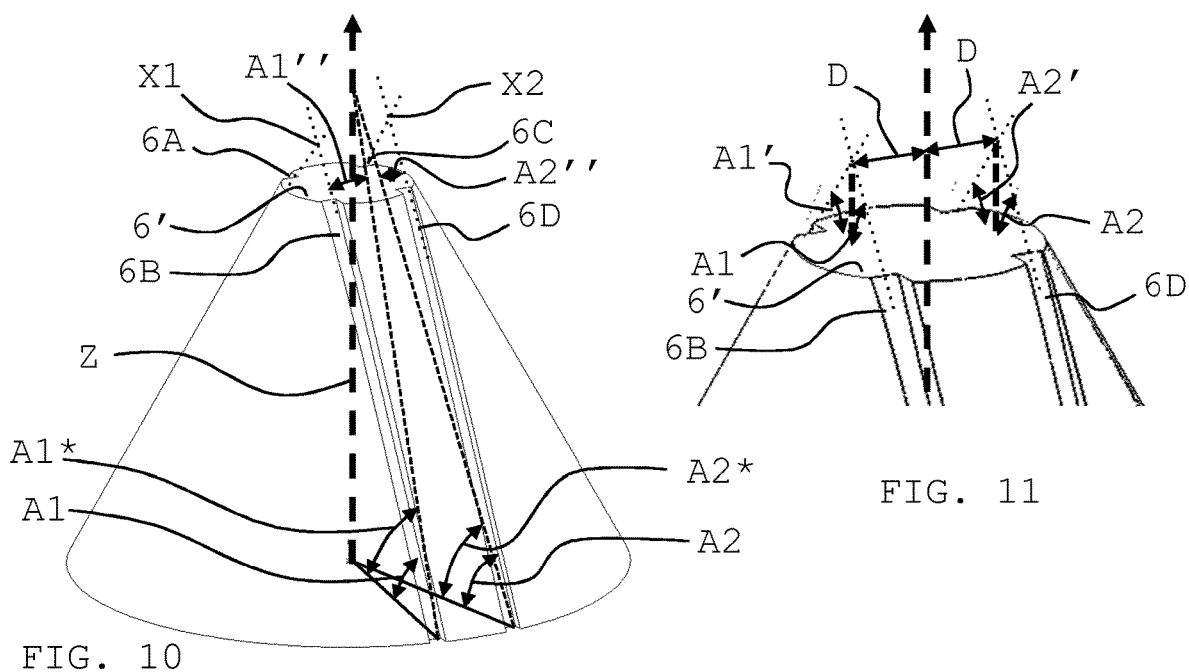
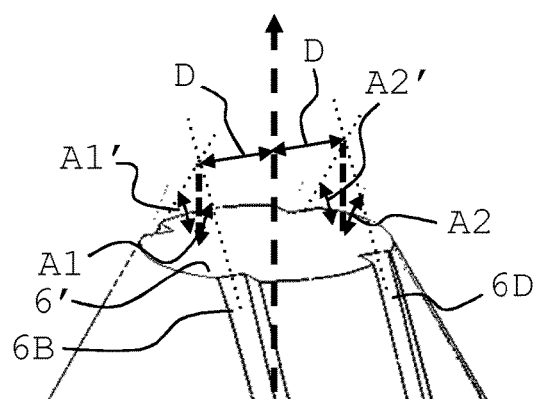
FIG. 10
FIG. 11

AEROSOL DELIVERY OF PIRFENIDONE

CROSS-REFERENCE TO RELATED APPLICATIONS

This application is a United States Application under 35 U.S.C. § 371 claiming priority to and the benefit of PCT Application No. PCT/EP2018/066719, filed Jun. 22, 2018, which claims priority to and the benefit of European Application No. 17177459.9, filed on Jun. 22, 2017, and U.S. Provisional Application Ser. No. 62/523,581, filed on Jun. 22, 2017, the contents of each which are hereby incorporated by reference in their entirety.

BACKGROUND OF THE INVENTION

Nebulizers or other aerosol generators for liquids are known from the art since a long time ago. Amongst others, such devices are used in medical science and therapy. There, they serve as inhalation devices for the application of active ingredients in the form of aerosols, i.e. small liquid droplets embedded in a gas. Such an inhalation device is known, for example from the document EP 0 627 230 B1. Essential components of this inhalation device are a reservoir in which the liquid that is to be aerosolized is contained; a pumping unit for generation of a pressure being sufficiently high for nebulizing; as well as an atomizing device in the form of a nozzle. A pumping unit is defined as a unit or device component capable of moving or compressing a fluid material and that comprises at least one pumping chamber, and optionally further comprises auxiliary components as well, such as a body, interfaces, and the like. By means of the pumping unit, the liquid is drawn in a discrete amount, i.e. not continuously, from the reservoir, and fed to the nozzle. The pumping unit works without propellant and generates pressure mechanically.

A known embodiment of such an inhalation device is presented in document WO 91/14468 A1. In such a device, the pressure in the pumping chamber which is connected to the housing is generated by movement of a moveable hollow piston. The piston is moveably arranged inside the immobile pumping chamber. The (upstream arranged) inlet of the hollow piston is fluidically connected to the interior of the reservoir (reservoir pipe section). Its (downstream arranged) tip leads into the pumping chamber. Furthermore, a check valve that inhibits a back flow of liquid into the reservoir is arranged inside the tip of the piston.

For filling the piston, the same is directly connected with its upstream end to the reservoir. By pulling out the piston of the pumping chamber, its interior volume is enlarged, such that an increasing under pressure is built up inside the pumping chamber. This pressure propagates through the hollow piston into the reservoir, such that liquid is sucked from the same into the piston. At the same time, said valve opens at its tip, since the pressure inside the reservoir is higher than inside the (yet empty) pumping chamber. The pumping chamber is being filled. At the same time, a spring is loaded, and locked at the motion's end when the moveable piston has reached its lower dead center and the pumping chamber is filled.

The spring can be manually unlocked. The stored energy is then abruptly released. The piston is again pushed in direction of the pumping chamber and into the same, thus decreasing its interior volume. The aforementioned check valve is now closed, such that a growing pressure builds up inside the pumping chamber, since the liquid is inhibited from flowing back into the reservoir. Eventually, this pressure results in ejection of the liquid from the nozzle which is arranged at the downstream end of the pumping chamber.

In order to face the risk of a reverse flow of already ejected liquid or even outside air, a further check valve, subsequently being called outlet valve, can be arranged at the downstream end of the pumping chamber just before the nozzle, allowing emitted liquid to pass, but blocking incoming gas.

The piston is arranged inside the pressure spring which is designed as helical spring, thus limiting its outside diameter. Also because of the typically small volume (e.g. 15 µl), the piston is designed with a thin interior (and often also exterior) diameter.

This typically small inner diameter of the moveable piston (e.g. 0.3 to 1.0 mm), together with a small size of the check valve being arranged within, is a drawback of the described construction. The small diameter results in a high flow resistance, such that in particular, media of higher viscosities flow into and through the piston only very slowly. In other words, the described construction is suitable especially for low-viscosity (aqueous) liquids and for emitting low doses thereof. Furthermore, fabrication of a sufficiently tight check valve of small diameter is difficult.

The compound pirfenidone (5-methyl-1-phenyl-2-(1H)-pyridone) is an anti-fibrosis and anti-inflammatory drug compound which has found use in particular in the prevention and treatment of fibrotic diseases and conditions such as pulmonary fibrosis. Oral products of pirfenidone, indicated for the treatment of idiopathic pulmonary fibrosis however have been associated with adverse effects, in particular effects such as dermal photosensitivity, gastrointestinal or hepatic issues. Local administration to the lung by inhalation of an aerosolized formulation of the drug substance may avoid these systemic effects of the oral product.

The prior art describes formulations comprising pirfenidone for inhalative use, for example in U.S. Pat. No. 9,517,204, which discloses powder formulations of pirfenidone which may be used for inhalative administration.

The document WO 2012/010638 describes formulations of pirfenidone or a pyridone analog compound suitable for aerosol administration such as by mist, gas-liquid suspension, liquid nebulized, dry powder and/or metered-dose inhaled aerosol administration. Liquid nebulizers, high efficiency liquid nebulizers, metered dose inhalers, and dry powder inhaler devices are described to be potentially applicable devices for dispensing the formulations. In particular, aerosol analysis studies using aqueous solutions of pirfenidone and liquid nebulizer devices are also described in this document. Liquid nebulizers, however, rely on a continuous delivery to a subject of a medicinally compositions, and typically rely on longer periods of administration and as well as require higher device-loads of liquid medicament in order to achieve a targeted dosing in the subject of the active ingredient. The relatively long duration of administering a single dose using conventional nebulization is a burden to the patient and thus a disadvantage of this delivery technology.

Inhalation devices based on the principle of aerosol generation by impingement of two streams of liquid ejected from a nozzle combines some of the advantages of common nebulizers with those of metered dose inhalers. A device of this category, comprising basic features such as a reservoir in which the liquid that is to be aerosolized is contained; a pumping unit for generation of a pressure being sufficiently high for nebulizing; as well as an atomizing device in the form of a nozzle, and which is able to release discrete amounts of an atomized liquid medicament is described for example also in U.S. Pat. No. 5,964,416. This document describes a device for atomizing fluids such as a aqueous or ethanolic solutions of pharmaceutical compositions to an inhalable aerosol. The amount of aerosol that can be discharged by said device is however only about 15 microliters. An inhalation device which only allows for a relatively small volume to be discharged per actuation may be limited, in terms of practicality and feasibility, for use in the administration of drug compositions where the delivery of relatively larger amounts of aerosolized composition may be necessary, for example in order to provide an effective dose of a drug for therapy.

If the device of U.S. Pat. No. 5,964,416 were to be used for the aerosol delivery of larger volumes than it is currently used, this would inherently mean that the duration of aerosol emission per actuation would have to be prolonged from currently 1-2 seconds to substantially more than 2 seconds. However, this would make the inhalation of the emitted aerosol by the patient in one single breathing manoeuvre difficult. Alternatively, increasing the volume flow of liquid to, or through, the nozzle by increasing the driving force or using ejection channels with larger diameters will cause technical difficulties and may not lead to the same aerosol quality.

It is an object of the present invention to provide an improved method for delivering pirfenidone to a patient by inhalation that overcomes one or more of the disadvantages of currently known inhalation therapies used for this drug. It is a further object to provide an inhalation device that enables such improved delivery method. Further objects of the invention will be clear on the basis of the following description of the invention, examples and claims.

SUMMARY OF THE INVENTION

In a first aspect, the invention relates to an inhalation device for the generation of an aerosol, the device comprising at least one reservoir containing a liquid composition comprising pirfenidone, wherein the inhalation device is a pump-actuated inhaler adapted to release upon actuation a metered dose of the liquid composition from the reservoir through a nozzle having at least three ejection channels adapted to eject the composition along respective ejection trajectories, and wherein at least one collision point is provided at which at least two of said ejection trajectories intersect with one another. In another aspect, the present invention provides for a reservoir containing a liquid composition comprising pirfenidone, wherein the reservoir is adapted for use with an inhalation device according to the inhalation device as defined in the embodiments described herein. In a further aspect, the invention relates to an inhalation device according to the first aspect and as defined in the embodiments described herein, for use the treatment or prevention of a lung disease or condition, preferably pulmonary fibrosis. In yet a further aspect, the invention provides an improved method of delivering pirfenidone to a subject according to which an inhalation device as describe above is used for the administration of a liquid composition comprising pirfenidone. In yet a further aspect, the invention provides a method of treating a subject which is based on such improved method delivering pirfenidone.

DETAILED DESCRIPTION OF THE INVENTION

The objects are solved by the subject-matter of the independent claims. Advantageous embodiments are described in the dependent claims, the subsequent description, as well as the accompanying figures.

Introductorily, some definitions of terms are given which are used throughout the description and claims. The definitions should be used to determine the meaning of the respective expressions unless the context requires a different meaning.

An "inhaler" or "inhalation device" is a device which is configured and adapted for the generation of an inhalable mist, vapor, or spray.

"Atomization" and "nebulization" in the context of inhalers means the generation of fine, inhalable droplets of a liquid. The typical dimensions of atomized droplets are in the range of several microns.

An "aerosol" is a dispersion of a solid or liquid phase in a gas phase. The dispersed phase, also termed the discontinuous phase, is comprised of multiple solid or liquid particles. The aerosol generated by the inhalation device of the invention is a dispersion of a liquid phase in the form of inhalable liquid droplets in a gas phase which is typically air. The dispersed liquid phase may optionally comprise solid particles dispersed in the liquid.

A "liquid" is a fluid material capable of altering its shape to that of a container which holds the liquid but retains a nearly constant volume independent of pressure.

A liquid may represent a monophasic liquid solution or a dispersion with a continuous liquid phase and a dispersed phase which may or may not be liquid.

A "plurality" means two or more.

"Interior" means inside, but also, oriented towards the inside; "Exterior" means outside, but also, oriented towards the outside.

A "nozzle" is a unit that serves for the atomization/nebulization of liquid. Generally, the term means the unit in its entirety. However, a nozzle can comprise one or multiple sets of individual, identical or different sub-units. A nozzle may have a plurality of ejection channels for emitting the liquid(s).

The "main axis" of a nozzle is its central axis parallel or collinear to the direction into which the bulk of the emitted aerosol travels after leaving the nozzle.

A "horizontal" plane is a plane that is perpendicular to the main axis.

The "ejection trajectory" is an imaginary and relatively straight line that starts at the end of an ejection channel. It resembles the initial travel path of a liquid emitted from the ejection channel when the inhalation device is operated. It is clear that the nozzle (and the entire inhalation device) must be adapted and configured by means of e.g. a suitable channel geometry and a sufficiently high pressure such that the emitted liquid can be provided in said straight line and with a sharp stream.

Where two or more ejection trajectories intersect, a "collision point" is formed.

A "collision angle" is the angle between the ejection trajectory and the main axis at the collision point. The "ejection angle" is defined as 90 degrees minus the angle ("intermediate angle I") between an ejection trajectory and a line that is parallel to the main axis and intersects with the ejection trajectory. If the collision point is located on the main axis, the parallel line is the main axis itself, and the intermediate angle is the collision angle. If the collision point is not the main axis, the parallel line is offset from the main axis. This "ejection offset" is the distance between the main axis and a collision point measured in a plane perpendicular to the main axis. The ejection angle may also be understood as the angle between an ejection trajectory and a line that is perpendicular to the main axis and connects the exit opening of the ejection channel with the main axis, if the respective collision point is on the main axis; if the respective collision point is not on the main axis, the ejection angle may also be understood as the angle between the ejection trajectory and a line that is perpendicular to the main axis and connects the exit opening of the ejection channel with a line that is parallel to the main axis and intersects with the ejection trajectory.

The term "metered dose" refers to the amount, for example as defined in terms of volume (e.g. microliter), of liquid composition that is releasable by the inhalation device as a result of a single (one) actuation of the device.

The term "a single dose" in reference to a composition refers to the complete amount of the composition administered to a subject in a dosing event, and which is pharmacologically active which is administered as part of a dosing regimen. As understood herein, a single dose may be administered to a subject, via a single (one) actuation of the inhalation device; alternatively it may also be administered over a plurality of actuations of the inhalation device, for example 2, or 3, or 4 actuations of the device, and in accordance with the prescribed usage, whereby the metered doses released per individual actuation combine to provide the required single dose.

Further definitions are provided in the subsequent description.

In a first aspect, the present invention relates to an inhalation device for the generation of an aerosol, wherein the device comprises at least one reservoir containing a liquid composition comprising pirfenidone, and wherein the inhalation device is a pump-actuated inhaler adapted to release upon actuation a metered dose of the liquid composition from the reservoir through a nozzle having at least three ejection channels adapted to eject the composition along respective ejection trajectories, and wherein at least one collision point is provided at which at least two of said ejection trajectories intersect with one another.

The inhalation device according to the invention serves for the generation of an aerosol of liquid composition comprising pirfenidone, in particular, of such aerosols which can be inhaled by a subject, e.g. a human subject, in need thereof. Preferably, the inhalation device is suited to be hand-held and/or portable, and may also be used by the individual subject themselves, following prescribed instructions.

The inhalation device is pump-actuated inhaler which as understood herein is an inhalation device comprising a mechanically driven pump device or unit that is capable of displacing or compressing a liquid and/or fluid, such as a liquid composition comprising pirfenidone according to the present invention. In one embodiment of the invention, the pump-actuated inhaler is a piston-pump actuated inhaler.

The pump-actuated inhaler may comprise a pump device or unit which generates a desired pressure for releasing the composition, such as in the present aspect, through a nozzle with at least three ejection channels, generating an aerosol. By means of the pumping unit, the liquid is drawn in a discrete amount, i.e. not continuously, from the reservoir, and fed to the nozzle. The pumping unit works without propellant and generates pressure mechanically. The pump unit or device preferably comprises of a pumping chamber, and a means for the storage of potential energy, the device being coupled to the pumping chamber and being lockable in a loaded position, wherein upon unlocking, the stored energy is transformable into a motion of the pumping chamber. A spring, but also gas or a magnetic force utilizing material can be used as means for the storage of potential energy.

The nozzle of the inhalation device according to the first aspect has a main axis and at least three ejection channels adapted to eject liquid along respective ejection trajectories, wherein at least one collision point is provided at which at least two of said ejection trajectories intersect with one another.

The main axis is parallel or collinear to the direction along which the aerosol generated from the liquid(s) is emitted from the inhalation device towards the user. The main axis can also be a rotation axis of the nozzle body.

Each of the ejection channels has its own ejection trajectory, i.e. a direction along which the respectively emitted liquid stream leaves its channel. Essentially, the trajectory is a relatively straight line, at least initially, or from the exit opening of the respective ejection channel to the corresponding collision point. It is clear that the parts of said channel which are further away from the exit opening (i.e. inside the nozzle body) can follow directions that are different from said ejection trajectory. It is also clear that liquid which is further away from the nozzle surface will deviate from said straight line, since the impulse is increasingly reduced, and the influence of air resistance and gravity become stronger. The orientation of the latter is primarily defined by the channel orientation directly at the respective exit opening. However, it can also be influenced by the exact shape of the exit opening, as well as deflectors or the like which may optionally be arranged directly behind the exit opening to redirect the emitted fluid.

At the collision point, at least two of said trajectories intersect, such that a collision-type (or impingement-based) aerosol formation is achieved. Since, according to the invention, at least a third ejection channel is present, said channel can also be directed at said collision point, such that a larger amount of liquid can be atomized, or the third channel can be directed away from said collision point, e.g. against a baffle or the like, such that a second collision point is formed.

Having the third ejection channel enables a larger amount of liquid to be atomized and consequently administered for inhalation. This is an advantageous, as it allows the inhaler device to be used for the delivery of active ingredients, which may require relatively larger doses for therapeutic efficacy and which also have relative poorer solubility in the preferred carrier, water, and which consequently may require a larger formulation volume, in order to achieve therapeutically relevant or applicable concentrations. Pirfenidone is one such drug falling into such category. In the context of the present invention, the presence of third ejection channel enables a larger volume of the liquid composition comprising pirfenidone to be aerosolized and administered effectively, and provide greater flexibility in the optimization of dosing parameters thereof.

Preferably, the inhalation device according to the invention and the embodiments described herein releases a metered dose of the liquid composition released upon actuation has a volume of at least about 20 μL (microliter). In a further embodiments, the metered dose of the liquid composition released upon actuation of the inhalation device is at least 18 μL, or at least 25 μL, 30 μL, or 50 μL. In other embodiments, the metered dose of the liquid composition released upon actuation has a volume of between 20 to 150 μL, or 25 to 250 μL, or 50 to 300 μL. Such volumes are generally difficult to achieve in devices where only two ejection channels are present in the nozzle.

In another embodiment of the invention, a single dose of the liquid composition comprising pirfenidone may be released by a one (single), or a plurality of actuations of the inhalation device. Preferably, the inhalation device is configured for a plurality of actuations i.e. for the release of multiple metered doses.

In one embodiment of the invention, the inhalation device according to the invention releases a single dose of the liquid composition comprising pirfenidone in a plurality of actuations of device, preferably two, three or four actuations of the device, or in accordance to prescribed usage or prescribed dosing.

Preferably a single dose of the liquid composition comprises an amount of at least 5 mg of pirfenidone. In other embodiments, the liquid composition comprises pirfenidone an amount of at least 4 mg, or at least 6 mg, or at least 8 mg, or at least 10 mg of pirfenidone. In yet further embodiments, the single dose of the liquid composition comprises an amount of pirfenidone in the range of 4 to 8 mg, 5 to 10 mg, 5 to 15 mg.

In another embodiment of the invention, the inhalation device comprises four ejection channels adapted to eject the composition along respective ejection trajectories, wherein two collision points are provided, and wherein at each of the two collision points, two of said ejection trajectories intersect with one another.

As noted above, greater metered dose volumes released are one of the advantages in having at least three, and also greater than three, such as four ejection channels which are adapted to eject the composition along respective ejection trajectories and providing at at least two collision points. Additional advantages are also provided by having more than one, or a plurality of collision points and are further discussed below.

In a further embodiment, the inhalation device comprises a housing, which preferably can be held comfortably with one hand. Arranged inside this housing, and optionally connected or connectable with the same, is at least one reservoir for storing at the liquid composition comprising pirfenidone, and at least one pumping unit with at least one pumping chamber for generation of a pressure inside said pumping chamber, wherein the at least one pumping chamber is fluidically connected with the at least one reservoir, optionally by means of at least one reservoir pipe (or reservoir pipe section(s)), via at least one check valve which blocks in direction of the reservoir(s). Thus, the at least one check valve allows a liquid flow from the reservoir(s) into the pumping chamber(s), and blocks a flow in opposite direction.

The inhalation device further comprises at least one riser pipe having at least one reservoir-facing, interior end which can be received in said pumping chamber, and a nozzle (or nozzle set) which is connected liquid-tight directly or indirectly to (an) exterior end(s) of the riser pipe(s).

The interior volume of the at least one pumping chamber is changeable by means of relative motion of the pumping chamber to the riser pipe(s) in that each riser pipe increases the volume by being pushed into, and decreases the volume by being pulled out of its respective pumping chamber. The term "interior volume" describes the volume which extends from the reservoir-facing inlet of each pumping chamber to the place where the interior end of the respective riser pipe is located.

In one embodiment of the invention, each riser pipe is immobile and firmly, directly or indirectly, and/or permanently or detachably, attached to the housing, while each pumping chamber is moveable relative to the housing. In other words, each riser pipe maintains its position relative to the housing, and each pumping chamber can alter its position relative to the housing, and in particular, along a longitudinal axis of the same, such as to perform a piston-in-cylinder-type movement of the immobile riser pipe in the moveable pumping chamber.

In another embodiment, the immobility of each riser pipe is primarily related to the nozzle, rather than to the housing. Thus, nozzle and riser pipe(s) form—in terms of movability—one unit. However, if the nozzle itself is immobile with respect to the housing, this is also true for the riser pipe(s), thus arriving at the firstly described embodiment.

An advantage of these features is that the passage(s) between pumping chamber(s) and reservoir(s) can be designed with less restrictions compared to the known art. It is, for example possible to design a significantly larger check valve, which is easier to manufacture, since it does not have to be contained within the hollow piston known from the art. As a result, the size of the respective check valve is mainly only restricted by the interior size of the housing or, if such a construction is desired, the inner size of a spring that surrounds the pumping unit(s). The (approximate) identity of the diameter of valve, riser pipe and reservoir pipe, as known from the art, becomes obsolete. Furthermore, since no movable piston needs to be connected to the respective reservoir, the component which enters the reservoir(s) and the moveable component (i.e. the pumping chamber(s)) can be designed independent of each other, allowing to better suit the individual functions. In this respect, the invention provides for higher design flexibility because the at least one moveable pumping chamber, due to its robust structure and dimensions, provides better opportunities for designing a mechanically stable connection with the reservoir(s) than does the respective moveable riser pipe which is typically less robust. Also, the connection between pumping chamber(s) and reservoir(s) can be designed with a larger diameter, such that higher flow velocities and fluid viscosities become feasible. Further, a mechanical support for the reservoir(s) can be integrated into the component that comprises the pumping chamber(s). Additionally, the vent for pressure equilibration of the reservoir(s) can be moved away from the reservoir body itself to, e.g., a connector which forms an interface between reservoir(s) and pumping chamber(s), facilitating the construction and avoiding the necessity to provide an essentially "open" reservoir body.

In both of the aforementioned embodiments, the nozzle has a main axis and at least three ejection channels adapted to eject liquid along respective ejection trajectories, wherein at least one collision point is provided at which at least two of said ejection trajectories intersect with one another.

The main axis is parallel or collinear to the direction along which the aerosol generated from the liquid(s) is emitted from the inhalation device towards the user. The main axis can also be a rotation axis of the nozzle body.

Each of the ejection channels has its own ejection trajectory, i.e. a direction along which the respectively emitted liquid stream leaves its channel. Essentially, the trajectory is a relatively straight line, at least initially, or from the exit opening of the respective ejection channel to the corresponding collision point. It is clear that the parts of said channel which are further away from the exit opening (i.e. inside the nozzle body) can follow directions that are different from said ejection trajectory. It is also clear that liquid which is further away from the nozzle surface will deviate from said straight line, since the impulse is increasingly reduced, and the influence of air resistance and gravity become stronger. The orientation of the latter is primarily defined by the channel orientation directly at the respective exit opening. However, it can also be influenced by the exact shape of the exit opening, as well as deflectors or the like which may optionally be arranged directly behind the exit opening to redirect the emitted fluid.

At the collision point, at least two of said trajectories intersect, such that a collision-type (or impingement-based) aerosol formation is achieved. Since, according to the invention, at least a third ejection channel is present, said channel can also be directed at said collision point, such that a larger amount of liquid can be atomized, or the third channel can be directed away from said collision point, e.g. against a baffle or the like, such that a second collision point is formed.

According to one embodiment, preferably, each ejection trajectory intersects with at least one other ejection trajectory. This means that there is no ejection trajectory which does not intersect with another one, but every ejection trajectory hits at least one other ejection trajectory. Accordingly, in case of three channels, all ejection trajectories collide in one common collision point. In case of four channels, one or two collision points can be present.

According to a preferred embodiment, the inhalation device comprises further a means for the storage of potential energy, the device being coupled to the pumping chamber and being lockable in a loaded position, wherein upon unlocking, the stored energy is transformable into a motion of the pumping chamber. A spring, but also gas or a magnetic force utilizing material can be used as means for the storage of potential energy. One end of the means is supported at or in the housing at a suitable location; thus, this end is essentially immobile. With the other end, it is connected to the pumping chamber; thus, this end is essentially moveable.

According to one embodiment, the check valve is adapted to open only when the pressure difference between the upstream and the downstream side of the valve, i.e. the reservoir and the pumping chamber side, is above a predefined threshold value, and remains closed as long as the pressure difference is below the threshold value. “Pressure difference” means that, irrespective of the concrete pressure values, only the relative pressure difference between the two sides is relevant for determining whether the check valve blocks or opens.

Only upon activation of the pumping device, by building up a high pumping chamber pressure, the pressure difference (due to a high pressure in the pumping chamber, and a significantly lower pressure in the reservoir, resulting in a large pressure difference) becomes high enough and exceeds the threshold value of the pressure difference, so that the check valve finally opens and allows the pressure chamber being filled with liquid from the reservoir.

According to a further embodiment, an inhalation device comprises an outlet valve inside the riser pipe for avoiding a return flow of liquid or air into the exterior end of the same.

According to another embodiment, the inhalation device comprises an outlet valve between riser pipe and nozzle for avoiding a return flow of liquid or air towards the exterior end of the riser pipe.

Optionally, the outlet valve can be of a type that blocks below (and opens above) a threshold pressure difference as described above.

According to one embodiment, all ejection angles at which the individual trajectories leave the nozzle are identical with respect to the main axis, and, typically, with respect to the front surface of the nozzle (if essentially flat, and perpendicular to the main axis). Thus, if all channels are arranged symmetrically around said main axis, one common collision point can be provided. In this context, a symmetric arrangement around the main axis means that the exit openings of all channels are in the same plane perpendicular to the main axis and also positioned at the same distance to the main axis. In this case, a common collision point for all trajectories may be provided at the intersection of the trajectories with the main axis. In such embodiment, the nozzle preferably exhibits three or four channels in total.

Such a common collision point can be obtained e.g. when all individual trajectories are placed on the surface of a truncated cone, with the intersection of all trajectories at the virtual tip of the truncated cone. If the ejection trajectories lie in a common plane, i.e. in a two-dimensional setup, by using identical angles, more than one collision point can be provided.

According to another embodiment, again with respect to the nozzle’s main axis, in a setup where the lateral distances between main axis and channel exit openings are identical, at least one—and preferably at least two—of said ejection angles differ(s) from the others, such that different collision points can be provided. Using the example of a truncated cone again, by use of four ejection channels, it is possible to provide a nozzle with two collision points, wherein a first pair of channels provides a first, and a second pair of channels provides a second collision point, one or both being laterally offset from the virtual tip of the truncated cone. In this case, not all the ejection angles are the same with respect to the main axis (e.g. of the truncated cone). Optionally, each of the two ejection trajectories corresponding to the first pair of channels exhibit a first ejection angle, and each of the two ejection trajectories corresponding to the second pair of channels exhibit a second ejection angle, wherein the first ejection angle is different from the second ejection angle. If the exit openings of all channels are positioned symmetrically around the main axis (with the same lateral distance to the main axis), such configuration will result in two collision points, namely a first collision point at the intersection of the two trajectories corresponding to the first pair of channels with the main axis and a second collision point at the intersection of the trajectories corresponding to the second pair of channels with the main axis.

In contrast, in a two-dimensional setup, by selecting different ejection angles, all ejection trajectories can be directed to the same collision point. Preferably, the channels are arranged in a symmetrical manner such that there exists a (“vertical”) plane in which the main axis lies which virtually divides the nozzle in two mirroring halves. For each trajectory, the collision angle, which is the angle between the ejection trajectory and the main axis at the collision point, preferably ranges from 15° (sharp angle) to 75° (obtuse angle), and lies more preferably in the range between 30° and 60°; an angle of approximately 45° is also considered to be particularly preferred.

In one embodiment, at least two collision points are provided, wherein each collision point is formed by at least two ejection trajectories having the same ejection angle. Thus, two ejection channels have a first, and two other ejection channels have a second ejection angle differing from the first one.

In another embodiment, the ejection angles differ one from the other, but the respective ejection trajectories still intersect, thus providing one collision point. This is, for example, the case when the nozzle surface is inclined with respect to the main axis, or when the nozzle surface is not planar.

One advantage of the embodiments with a collision point that is fed by more than two (and preferably all) ejection channels is that a larger amount of liquid can be nebulized without having to enlarge the cross sections of the individual ejection channels. Thus, the fluidic parameters of each channel can be left untouched, simply by adding additional channels.

An advantage of embodiments with a plurality of collision points is that by providing more than one collision point, in particular when larger quantities of liquid are nebulized, the risk of large droplet formation can possibly be reduced, because under certain circumstances, a too high concentration of liquid in one location (=collision point) can promote formulation of undesired large droplets. By separating one big collision point into two (or more) smaller collision points, the quantity of liquid required for nebulization at each individual collision point is significantly smaller.

Also, if a plurality of collision points is provided, each of these can be fed by liquid streams of individual liquids which differ between the collision points. Thus, no mixing of these liquids takes place until the completion of the atomizing phase, which can be advantageous for certain liquids that should not come into contact with each other.

According to another embodiment, along the nozzle's main axis, at least two, or even all collision points are located within the same perpendicular plane, i.e. perpendicular with respect to the main axis. This means that the distance between each collision point and the front surface of the nozzle is essentially the same. This can be advantageous when the individual nebulized liquids (sprays, mists) are approximately of the same size and shall be inhaled as parallel volumes.

In another embodiment, along the nozzle's main axis, at least two or even all collision points are on different perpendicular planes. This means that the distances of at least two collision points with respect to the front surface of the nozzle are different.

If the e.g. two collision points are both located on the main axis, it is possible to produce a central aerosol stream from a first liquid, and a surrounding sheath stream of an aerosol of a second liquid. Such a core-and-sheath stream can advantageously be used for inhalation purposes if e.g. one component of the stream (the sheath) is intended to be dispensed on the trachea, and another (the stream's core) in the bronchioles.

According to another embodiment, with respect to the nozzle's main axis, all collision points are located on the main axis (symmetric setup). This means that, if a plurality of collision points is present, they are located in parallel planes, where the main axis intersects said plane(s). At the same time, when viewed in direction of the main axis, only one collision point is visible.

In another embodiment, at least one collision point is laterally offset from the main axis (asymmetric setup). This means that, when viewed in direction of the main axis, more than one collision point is visible, one or all collision points being laterally displaced from the main axis. The collision points can then lie on different planes, or they can be situated on one common plane.

According to one embodiment, all of the nozzle's ejection channels have the same cross section. Such an embodiment is particularly useful when only one liquid, or several liquids of similar physical parameters and in comparable amounts, shall be atomized.

In another embodiment, at least one nozzle's ejection channel, or ejection channel pair, has different cross sections than another ejection channel, or ejection channel pair. In other words, the cross sections of individual channels or pairs of channels differ from each other. Such a setup is advantageous when two or more liquids shall be atomized that have differing physical parameters and/or shall be atomized in differing amounts.

With respect to all embodiments described above in which a plurality of collision points is provided, a preferred total number of collision points is two or three, and in particular two.

According to one embodiment, all of the nozzle's ejection channels are connected to the same pumping chamber or liquid type reservoir, such that all collision points can be fed with the same liquid. That means that regardless of the number of ejection channels, only one liquid is atomized by the nozzle. Then, preferably, all ejection channels are of the same dimensions, since the type of liquid is the same for all channels.

If the inhalation device has more than one pumping chamber or pumping unit, all pumping chambers or pumping units are connected to the same reservoir, or to reservoirs that hold the same liquid type.

If the inhalation device has just one pumping chamber, it can be fed with the liquid from one or more reservoirs. It then serves as mixing chamber as well, before the liquid is fed to the nozzle.

According to another embodiment, at least two of the nozzle's ejection channels are connected to individual pumping chambers or liquid reservoirs, such that at least one collision point which can be fed with a different liquid composition (i.e. a second liquid whose composition is different from the first or previously mentioned liquid) is provided. Thus, such a setup is useful for the generation of more than one aerosol at the same time. It is clear that in this case, each liquid must have its own pumping chamber in order to avoid undesired mixing. It is also clear that each pumping chamber must be connected to an individual reservoir, or that at least two pumping chambers must be connected to individual reservoirs such that at least two different liquids can be atomized.

It should be noted that even when only one liquid is to be atomized, an inhalation device having a plurality of pumping chambers and/or reservoirs can be advantageous. The amount of liquid that can be put under pressure with a single pumping chamber may be limited; thus, by increasing the number of pumping chambers, more liquid can be atomized. Also, the geometry of a reservoir can be standardized. Thus, one inhalation device that receives such standardized reservoirs can be used for the generation of a mixture of individual liquids as well as a "mixture" of the same liquid stemming from a plurality of reservoirs. Further, the mixing ratio of different liquids can easily be adapted simply by using the desired number of reservoirs filled with the individual liquids. For example, if one liquid comprises a medically active agent, and another liquid is a solvent or diluting agent, and the housing holds three reservoirs, a ratio of agent:diluent of 1:1 (one dummy reservoir), 1:2, or 2:1 is possible.

In another embodiment, at least two of the nozzle's ejection channels are connected to a common mixing chamber arranged upstream of the channels and downstream of the respective reservoirs. Such a mixing chamber is different from the aforementioned mixing by a common pumping chamber in that a separate volume is provided that is arranged between pumping chamber and nozzle, which has the purpose of mixing liquid from several (yet possibly also identical) sources before feeding them to the ejection channels.

According to one embodiment, at least two ejection channels of the nozzle form a pair (or group, in the case of three or more ejection channels) and share a common inlet as well as intersecting trajectories. Preferably, a pair or group of channels consists of two (or three or even more) channels of identical geometry, in order to obtain a most uniform atomizing result. A pair or group generates an aerosol in one collision point. Multiple pairs can share collision points, or each pair or group may have its own distinct collision point. These distinct collision points may be located at the same or at different horizontal planes.

In another embodiment, all ejection channels of the nozzle have individual inlets. Thus, they do not form pairs, since a pair is characterized by identical liquid flowing through the channels. However, they can still have ejection trajectories that intersect with each other such that one or more collision points are provided.

According to one embodiment in which two of the nozzle's ejection channels form a pair, one main feed channel is arranged to connect to the upstream end of the first ejection channel, and a cross channel exists that connects said main feed channel with the upstream end of the second ejection channel. The upstream end of the main feed channel is connected directly or indirectly via a pumping unit to a liquid reservoir. Such a construction is preferably realized in a two-dimensional setup, where all channels are located in the same plane.

The cross channel may have a perpendicular orientation with respect to said main feed channel; thus, the shortest possible fluidic connection is provided. The cross channel can also follow a different path, such as an arched path that might lie in a plane that is perpendicular to the main axis. The cross channel can also be offset to the plane in which the ejection channels of the respective pair are located; however, it is clear that in any case a fluidic connection between the cross channel and the corresponding ejection channels must be provided.

Since the two ejection channels of a pair are arranged on opposite sides with respect to the main axis, and since the cross channel connects the two ejection channels of a pair, only one (common) main feed channel is sufficient for this pair. Thus, only one inlet opening exists which must be coupled to a pumping chamber. In this way, a space saving solution is provided with respect to the amount of area that is necessary for connecting one pair of the nozzle to the upstream-arranged component.

In one embodiment of the inhalation device with a nozzle having a plurality of pairs, such as two pairs, the exit openings of the ejection channels of a first pair, with respect to the main axis which then also forms a (rotational) symmetry axis, are in a rotated position relative to the exit openings of the ejection channels of a second pair, e.g. 60° (or another integer factor of 360°), and the respective cross channels are, along said symmetry axis, spaced apart from one another, in order not to intersect with each other. In other words, the aforementioned cross channel construction is repeated for several times, e.g. duplicated or triplicated, and positioned apart from each other by rotating the respective unit comprising a pair of ejection channels, the corresponding cross channel, and the main feed channel around the main axis. If the individual cross channels are arranged on different planes along the main axis, the do not intersect with each other. The result is a turret-like arrangement of inlet openings for the different pairs (and thus, different liquids) which lie on a circular path, placed on the interface between the nozzle body and the component that feeds it with the liquid(s).

According to another embodiment, the nozzle exhibits a front side and a back side opposite to the front side. The front side, which is the face of the device which is oriented towards the user when the device is operated, comprises the exit openings of the ejection channels. The back side, or rear of the nozzle, which faces the interior of the device, is essentially flat and comprises a plurality of openings that form inlets to the main feed channel(s).

Preferably, the device component that connects to the back side of the nozzle is providing a corresponding surface with feed openings, so that each feed opening of said device component connects with an inlet opening of the nozzle. In other words, the interface between nozzle and the component that feeds the nozzle, e.g. the outlet sides of the pumping chambers, is designed such that a simple flat gasket is sufficient. Such a gasket essentially consists of a flat sheet of elastic material with holes at the appropriate positions.

The advantage of such a construction is that the fluid connection can be established safely and easily, and that the cost of providing a seal as well as the interface surfaces is low.

In some embodiments, the nozzle is constructed as a stack of relatively flat plates. Such plates can preferably be fabricated by material subtracting technologies such as etching or the like. Wafers of different materials such as silicon, glass, metal, ceramics, or plastics can form the semi-finished product. The channels are brought into one of the two flat sides of the substrate, or even on both sides. Then, by stacking several of such plates, a nozzle stack providing a plurality of ejection channel pairs can be fabricated.

In other embodiments, the nozzle is constructed from a three-dimensional rotation symmetric basic shape. Such a basic shape can be a cone, a cylinder, or a pyramid. Typically, the rotation or symmetry axis of the base shape coincides with the main axis of the finished nozzle.

In yet other embodiments, the inhalation device may be configured and adapted for the ejection of two (or more) liquids.

Therefore, the nozzle has at least two ejection channels, wherein these channels either can be fed with two (or more) different liquids, i.e. each of the channels receives a liquid that is different from the liquid fed to another channel, or they can be fed from a common mixing chamber which in turn is fed with these different liquids. Thus, ejection of two (or more) liquids is possible.

In order to achieve this, said ejection channels or said mixing chamber is/are connected either to the respective pumping chambers of upstream arranged individual pumping units, or to individual interior volumes (pumping chambers) integrated into one common pumping unit.

In other words, the inhalation device can comprise either a plurality of individual pumping units, each preferably serving the ejection of one liquid, or a construction is provided with a plurality of pumping chambers integrated into one main pumping unit (main pumping body), preferably being connected to only one means for the storage of potential energy (e.g. pressure spring). Each integrated pumping chamber may be connected to an individual liquid reservoir. The latter embodiment provides a more integrated and thus smaller solution.

According a further embodiment, the at least one reservoir is firmly attached to the pumping chamber and thus moveable inside the housing. This means that in each ejection cycle, the at least one reservoir moves together with the at least one pumping chamber from the initial position, in which the pumping chamber has its maximum interior volume, to the end position, in which the same is minimal, and eventually back to the initial position. As used herein, the expression "firmly attached" includes both permanent and non-permanent (i.e. releasable) forms of attachment. One of the advantages of this construction is that it provides the smallest possible dead volume between reservoir(s) and pumping chamber(s).

According to another embodiment, the at least one reservoir is connected to the at least one pumping chamber by means of one (or more) flexible element(s) such as e.g. a hose, and firmly attached to the housing. Thus, according to this embodiment, the reservoir does not move along with the pumping chamber, but is firmly (but, however, typically detachably) attached to the housing. One advantage of this construction is that the energy which is abruptly released upon unlocking the means for the storage of potential energy acts solely onto the pumping chamber for accelerating the same, but not also onto the reservoir which typically—and in particular at the beginning of its usage—can have a relatively large mass. A higher acceleration of the pumping chamber, and thus, a higher pressure, is the result.

In another aspect, the present invention relates to a reservoir containing a liquid composition comprising pirfenidone, wherein the reservoir is adapted for use with an inhalation device according to any one, or combination of device embodiments described above. The reservoir is adapted to be housed, and integrated with the other features and components of the inhalation device, and may be standardized where a plurality reservoirs may be contained and integrated in the inhalation device. Said reservoir is also connectable to the pumping chamber. In one embodiment, the reservoir (2) according to the invention is adapted to be firmly attachable to the pumping chamber (3) and is thus moveable inside the housing (1). In an alternative embodiment, the reservoir (2) is adapted to connect to the pumping chamber (3) by means of a flexible element, and firmly attached to the housing (1).

The amount of liquid composition comprising pirfenidone which may be accommodated, i.e. stored in the reservoir is an amount whereby on actuation of the device, an amount of at least one metered dose of the composition is released. Preferably, the reservoir is a multi-dose reservoir, meaning that it contains a plurality of single doses, which may be administered via a plurality actuations of the device. Alternatively expressed, the reservoir preferably contains an amount of the composition adapted for multiple, or a plurality of actuations of the inhalation device.

In one embodiment, the inhalation device and/or reservoir adapted for the inhalation device contains an amount of liquid composition comprising pirfenidone suitable for 1 to 20, or 1 to 30 or 1 to 60 actuations of the inhalation device, or an amount of liquid composition comprising pirfenidone suitable for the release of 1 to 20, or 1 to 30, or 1 to 60 metered doses of aerosolized composition.

The composition featured in the inhalation device according to the invention and embodiments described herein, comprises of pirfenidone (also known as 5-methyl-1-phenyl-2-(1H)-pyridone, under CAS No. 53179-13-8), an anti-fibrotic and anti-inflammatory compound. Studies have shown that pirfenidone acts by modulation of cytokines and growth factors which participate in fibrosis formation.

As understood herein, the term "comprising" and related terms "comprise" or "comprises" it is to be understood that features additional to the features prefaced by the term may be present. Conversely, the term "consists" and related terms would be understood as meaning that no other features, other than those prefaced by the term are present, and if present, only in trace or residual amounts such as to confer no technical advantage or relevance in respect of the object of the invention.

In the present invention, the compound pirfenidone is formulated as a composition that is suitable, and adapted for inhalative use, in other words a composition that may be atomized for inhalation and that is physiologically acceptable for inhalation by a subject. In an optional and alternative embodiment, the composition may comprise a salt, or a chemical structure analog of pirfenidone which has therapeutic equivalence to pirfenidone.

The liquid compositions comprising pirfenidone contained within the inhalation device and reservoir may be in the form of a dispersion, for example a suspension with a liquid continuous phase, and a solid dispersed phase. Preferably, however, the liquid composition is in the form of a solution.

In one embodiment, the liquid composition may comprise, optionally, one or more physiologically acceptable excipients, which are suitable for inhalative use. Excipients which may be featured in the composition include, but are not limited to buffering agents, salts, taste-masking agents, surfactants, lipids, and antioxidants. The liquid compositions are also essentially free of a propellant.

More preferably, the liquid composition is an aqueous solution, wherein pirfenidone is dissolved and solubilized in a liquid carrier solution comprising water. The aqueous solution optionally may comprise one or more excipients. Excipients may include, but are not limited to one or more buffering agents to regulate or control pH of the solution, salts, taste-masking agents, surfactants, lipids, antioxidants, and co-solvents, which may be used to enhance or improve solubility, for example ethanol, or a glycol. Preferably, the aqueous composition further comprises at least one buffering agent and/or a co-solvent.

A further aspect of the present invention relates to the use of the inhalation device in therapy and prophylactic treatment of respiratory disorders. In particular, the inhalation device according to the invention are used for the treatment or prevention of a lung disease or condition. As understood herein, a lung disease or condition may affect one or more anatomical aspect and/or function of a subject's lung(s) and associated respiratory airways.

Treatment refers to the administration of the liquid composition for the therapy of the lung disease or condition, for example leading to ameliorating, decreasing, or relieving of at least one symptom of the disease or condition, or stopping or slowing the progression of at least one symptom of the disease or condition, such as preserving lung function. The prevention of a lung disease or condition may be understood to be prophylactic treatment, and refers to the administration of the liquid composition to a subject that may not have developed the lung disease or condition but is at risk, or susceptible to the disease or condition.

In both the treatment or prevention of the lung disease or condition, the liquid composition is administered by means of the inhalation device and embodiments described herein at therapeutically effective amounts, such as in the amounts described above.

In a particularly preferred embodiment, the lung disease or condition is an interstitial lung disease affecting the interstitium of the lung and lung tissues such as those associated with the airways and air sacs (alveoli), for example pulmonary fibrosis, interstitial pneumonias, or sarcoidosis.

In further preferred embodiment, the inhalation device of the invention is used for the treatment or prevention of pulmonary fibrosis. In subjects affected by or diagnosed with pulmonary fibrosis, lung tissue scar formation and accumulation thereof (i.e. fibrosis) interferes with breathing ability. Fibrosis may occur inside the tissue, or between the airways and air sacs of the lungs, resulting in stiffer, and thicker tissue which hinders oxygen passage and diffusion. In administering pirfenidone, the inhalation device according to the invention and embodiments can be used for the preservation of lung function and/or to reduce rate of progression of pulmonary fibrosis in a patient diagnosed with said condition.

Pulmonary fibrosis may also develop as a secondary disease or condition to a primary diseases and conditions which may induce or result in fibrosis development in the lung tissues, for example such as another interstitial lung disease, an autoimmune disease, such as relating to connective tissues, environmental or occupational exposure, radiation exposure, viral or bacterial infections in the lung or genetic/inherited predisposition. Pulmonary fibrosis however often has no precise diagnosable cause.

Pulmonary fibrosis which is diagnosed or appears without a known cause is generally termed idiopathic pulmonary fibrosis. In a particularly preferred embodiment, the inhalation device containing a liquid composition comprising pirfenidone according to the invention is used for the treatment or prevention of idiopathic pulmonary fibrosis (often abbreviated as IPF).

Further within the scope of use of the invention is the treatment or prevention of diseases or conditions which are associated with, or which are a result of pulmonary fibrosis, such as lung clots, lung collapse, or lung cancer, respiratory failure, pulmonary hypertension, or heart failure.

In one embodiment of the invention, the inhalation device of the invention containing a liquid composition comprising pirfenidone, preferably an aqueous solution of pirfenidone, is used for the treatment or prevention of pulmonary fibrosis, wherein a metered dose volume of at least 20 ($\mu$L) microliter, of the composition is administered.

In another embodiment, the inhalation device of the invention containing a liquid composition comprising pirfenidone, preferably an aqueous solution of pirfenidone, is used for the treatment or prevention of pulmonary fibrosis, wherein a single dose amount of at least 4 to 5 mg of pirfenidone is administered, said single dose being administered in a single (one) actuation of the inhalation device, or alternatively, by a plurality of actuations of the device, for example, 2 to 4 actuations.

In other embodiments, said metered dose volume of the composition and/or said single dose amount of pirfenidone is preferably used for the treatment or prevention of idiopathic pulmonary fibrosis.

The use of an inhalation device or reservoir containing a liquid composition comprising pirfenidone, as described in any one of the above embodiments, in the manufacture or preparation of a medicament or medical device for the treatment of a subject in need thereof in relation to any one of preferred lung diseases or conditions are also provided for in the context of the present invention.

In yet a further aspect, the present invention relates also to a method of treating or preventing a lung disease or condition in a subject in need thereof, the method comprising a step of administering a metered dose of a liquid composition comprising pirfenidone using an inhalation device as described in any one or combination of the above embodiments.

In a further embodiment, the method of treating or preventing a lung disease or condition in a subject comprises a step of administering a metered dose of a liquid, composition comprising pirfenidone using an inhalation device as described in any one or combination of the above embodiments, wherein a single i.e. complete dose of the liquid composition comprising pirfenidone may be released by a one, or a plurality of actuations of the inhalation device, and optionally wherein the single dose of the liquid composition comprises an amount of at least 5.0 mg of pirfenidone. A plurality of actuations to administer a single dose may be performed for example through 2 to 4 actuations of the inhalation device.

Preferably the inhalation device used in the method is a handheld, i.e. portable device, whereby the administration of the composition and actuation of the device by the human subject or patient themselves directly and in accordance with prescribed instructions which may also accompany the device.

In a particularly preferred embodiment, the method relates to the treatment or prevention of a lung an interstitial lung disease affecting the interstitium of the lung and lung tissues such as those associated with the airways and air sacs (alveoli), for example pulmonary fibrosis, interstitial pneumonias, or sarcoidosis.

In further preferred embodiment, the method relates to the treatment or prevention of pulmonary fibrosis, wherein the method comprises a step of administering of a liquid composition comprising pirfenidone with an inhalation device according to the invention. In such an embodiment, the subjects are affected by or diagnosed with pulmonary fibrosis have accumulated lung tissue scarring (i.e. lung tissue with fibrosis) such as occurring inside the lung tissue, or between the airways and air sacs of the lungs and have poor oxygen diffusion.

Further embodiments may relate to a method of treating or preventing pulmonary fibrosis which develops as secondary disease or condition to a primary disease and conditions that induces or results in fibrosis development in the lung tissues, for example another interstitial lung disease, an autoimmune disease, such as relating to connective tissues, environmental or occupational exposure, radiation exposure, viral or bacterial infections in the lung or genetic/inherited predisposition. In yet a further embodiment, the method relates to a treatment or prevention of a disease or condition which is associated with, or which is a result of pulmonary fibrosis, such as lung clots, lung collapse, or lung cancer, respiratory failure, pulmonary hypertension, or heart failure.

In a particularly preferred embodiment, the method is directed to a treatment or prevention of pulmonary fibrosis which is diagnosed or appears without a known cause, i.e. idiopathic pulmonary fibrosis (IPF).

In a further aspect, the invention provides a method for delivering pirfenidone to a subject in need thereof, the method comprising the step of providing an inhalation device as described above to said subject. The subject is preferably a human patient, in particular a human patient suffering from a lung disease or condition, preferably an interstitial lung disease, such as pulmonary fibrosis, in particular idiopathic pulmonary fibrosis (IPF). The patient may further be provided with instruction to use the device, to actuate it and to inhale the aerosol emitted from it.

In yet a further aspect, the invention provides a method of treating a subject suffering from a lung disease or condition, preferably an interstitial lung disease, such as pulmonary fibrosis, in particular idiopathic pulmonary fibrosis (IPF), the method comprising a step of administering pirfenidone to said subject using a device as described above. Again, the patient may be provided with instruction to use the device, to actuate it and to inhale the aerosol emitted from it.

DESCRIPTION OF THE DRAWINGS

FIG. 7 shows a nozzle according to a first embodiment.

FIG. 8 shows a detail thereof.

FIG. 9 shows a nozzle according to a second embodiment.

FIG. 10 shows a nozzle according to a third embodiment.

FIG. 11 shows a detail thereof.

In FIG. 1, the main components of an inhalation device useful for carrying out the invention are depicted schematically and not-to-scale, at the situation prior to first use.

The inhalation device comprises a housing 1, which is preferably shaped and dimensioned such that it can be held with one hand and can be operated by one finger, e.g. the thumb (not shown). Two reservoirs 2A, 2B for the respective storage of a medically active liquid F1, F2 are located inside the housing 1. The depicted reservoirs 2A, 2B are designed to be collapsible; that means that during proceeding emptying, the elastic or at least limp walls buckle, so that the underpressure which is necessary for extraction of a certain amount of liquid F1, F2 is not, or almost not, increased. A similar effect can be achieved when a rigid container has a moveable bottom by means of which the interior volume of the respective reservoir can also be successively be reduced (not shown).

Further, the inhalation device comprises a pumping unit with two pumping chambers 3A, 3B within the housing 1 for generation of the desired pressures which are necessary for emitting liquid F1, F2 and nebulizing the same. The pumping unit can also comprise additional, not depicted components (push button, locking device, etc.).

The pumping chambers 3A, 3B can be present within separate pumping units, as shown in the present example, or they can be present as integrated into one single pumping unit (not shown).

Pumping chambers 3A, 3B are fluidically connected with reservoirs 2A, 2B by means of a respective inlet check valve 4A, 4B. Check valves 4A, 4B serve for allowing inflow of liquid F1, F2 into the respective pumping chamber 3A, 3B, and block a back flow of liquid F1, F2 into reservoir 2A, 2B upon release of the not-depicted locking mechanism.

As a means for the storage of potential energy 7, a spring is provided which is coupled with one (upwards directed) end to the pumping chambers 3A, 3B and which is supported at housing 1 (lower part of the figure).

The inhalation device further comprises two riser pipes 5A, 5B with at least one respective reservoir-facing, interior end 5A', 5B' which can be received in said pumping chambers 3A, 3B. In other words, riser pipes 5A, 5B can at least partially be pushed into pumping chambers 3A, 3B, resulting in a decrease of the interior volumes of pumping chambers 3A, 3B. The term "interior volume" describes that volume which extends from the reservoir-facing inlet of the pumping chamber 3A, 3B to the place where the interior end 5A', 5B' of the riser pipe 5A, 5B is located. In the depicted situation, riser pipe 5A, 5B is almost entirely contained in the respective pumping chamber 3A, 3B. As a result, the respective interior volume, situated between check valves 4A, 4B and the interior end 5A', 5B' of riser pipes 5A, 5B, is at a minimum.

Preferably, in the section which serves for the reception of the riser pipes, pumping chamber 3A, 3B has section with an circular inner cross section that corresponds to the (then also) circular outside cross section of the according riser pipe section. Of course, other cross section shapes are possible as well.

According to the depicted embodiment, check valve 4A, 4B is arranged between reservoir 2A, 2B and inlet of pumping chamber 3A, 3B.

Further, the inhalation device comprises a nozzle 6 which is connected liquid-tight to the respective exterior ends 5A", 5B" of riser pipes 5A, 5B. Nozzle 6 is suitable for nebulizing/atomizing liquid by using the principle of two colliding liquid jets. The nozzle 6 which is depicted as an example comprises two ejection channels 6A, 6B. At a time, each of the two nozzle's ejection channels 6A, 6B are connected to an individual pumping chamber 3A, 3B and thus, liquid reservoir 2A, 2B, such that a collision point which can be fed with a different liquids is provided. Each liquid F1, F2 has its own pumping chamber 3A, 3B in order to avoid undesired mixing.

Preferably, the cross sections of the liquid-containing channels are relatively small, and typically, in the region of microns. In the example, the angles of the ejection channels 6A, 6B with respect to the main axis Z (dashed line) are such that their ejection trajectories (dotted lines) intersect in one common collision point X.

Also depicted is an optional outlet valve 8A, 8B inside riser pipe 5A, 5B for avoiding back flow of liquid or air into the exterior end 5A", 5B" of the same from the outside. Outlet valve 8A, 8B is arranged in the interior end 5A', 5B' of riser pipe 5A, 5B. Liquid F1, F2 can pass outlet valve 8A, 8B in direction of nozzle 6, but outlet valve 8A, 8B blocks any undesired back flow in the opposite direction.

As can be seen in FIG. 1, riser pipe 5A, 5B is designed immobile and firmly attached to housing 1, indicated by the connection in the region of exterior end 5A", 5B" with housing 1. Riser pipe 5A, 5B is also firmly attached to nozzle 6, which in turn is attached to housing 1 as well. On contrary, pumping chamber 3A, 3B is designed to be moveable with respect to housing 1 and nozzle 6. The benefits of this design have already been explained; reference is made to the respective sections above.

Referring to FIG. 2, a device similar to the one of FIG. 1 is depicted. However, the embodiment shown in FIG. 2 lacks the (optional) outlet valves 8A, 8B. All other substantial components are present, and also the function is comparable.

FIG. 3, wherein some of the previously introduced reference numbers have been omitted for the sake of clarity, shows the embodiment of FIG. 1 just before initially filling the pumping chambers 3A, 3B. Pumping chamber 3A, 3B is pulled down, loading the means for the storage of potential energy 7. Outlet valve 8A, 8B is closed due to underpressure inside pumping chamber 3A, 3B, and check valve 4A, 4B is open to reservoir 2A, 2B. Increasingly collapsing walls of reservoir 2A, 2B allow its inside pressure remain nearly constant, while pressure inside pumping chamber 3A, 3B drops because of the upwards motion pulling pumping chamber 3A, 3B off riser pipe 5A, 5B, increasing the respective interior volume of pumping chamber 3A, 3B. As a result, respective interior volume of pumping chamber 3A, 3B fills with liquid F1, F2 from reservoir 2A, 2B.

Figure 1:
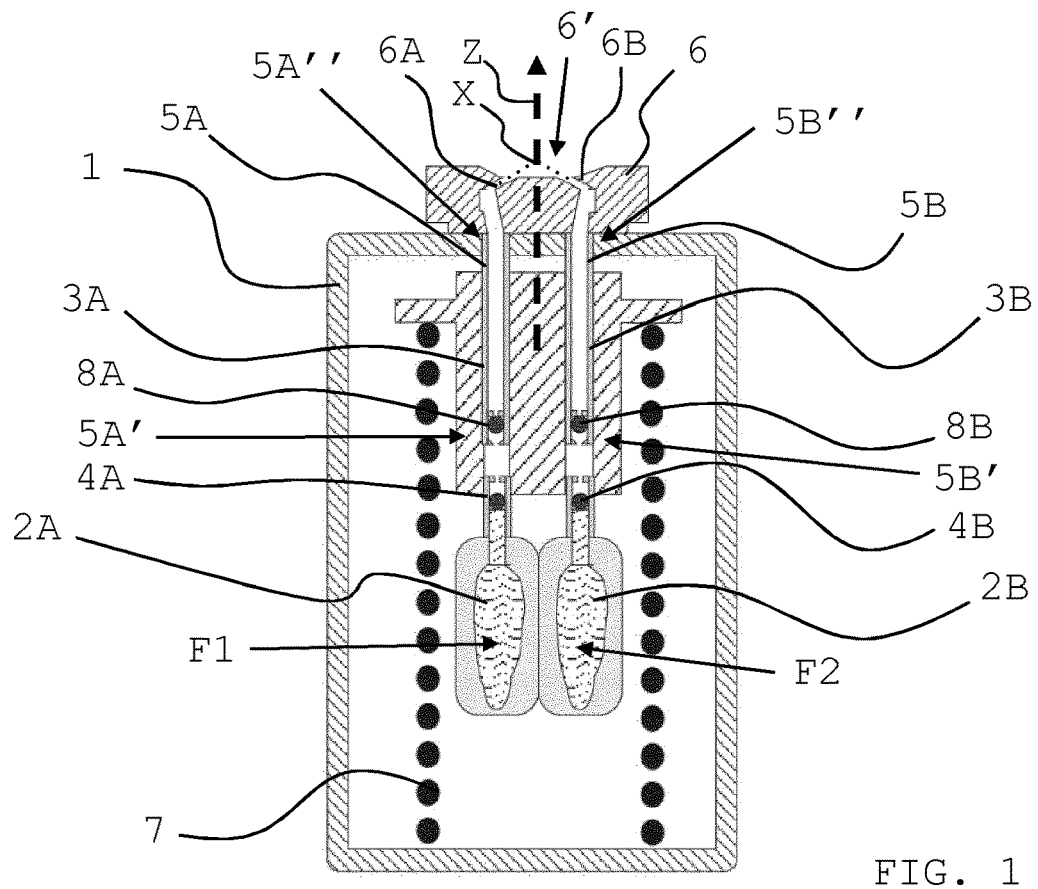
FIG. 1 shows the main components of an inhalation device useful for carrying out the invention.
Figure 2:
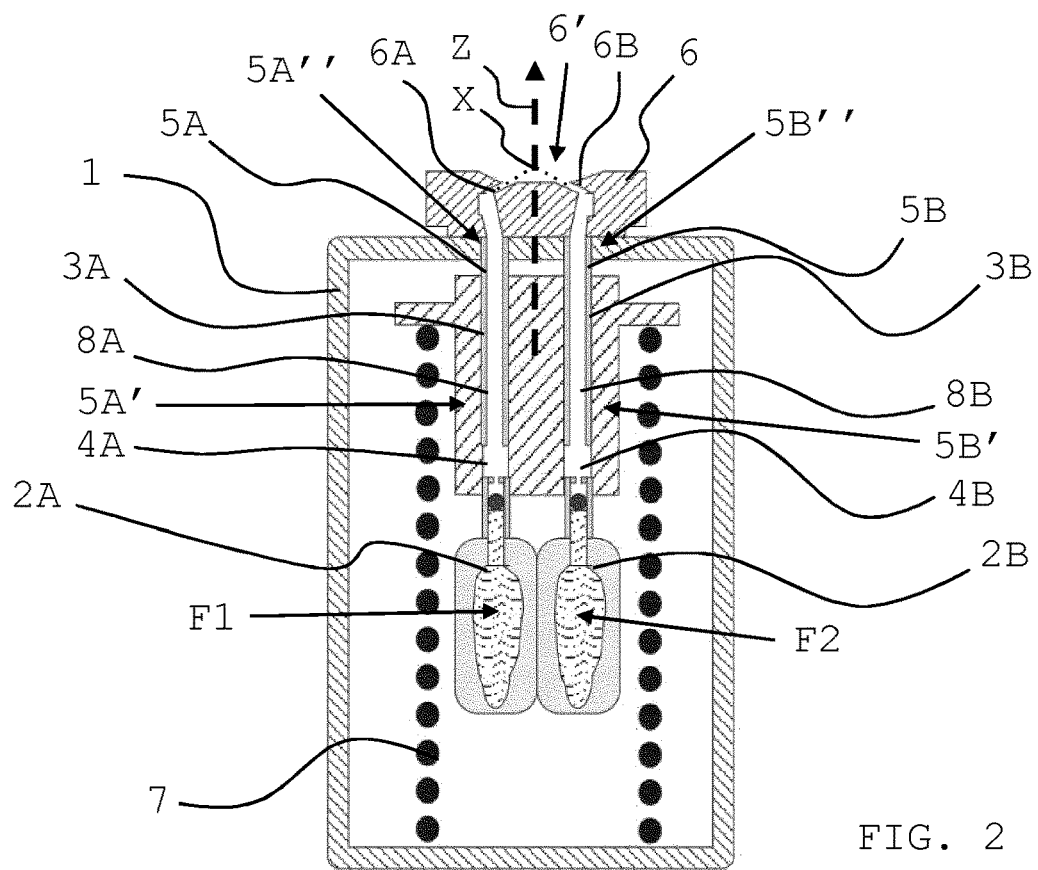
FIG. 2 shows a device similar to the one of FIG. 1, but without optional outlet valves.
Figure 3:
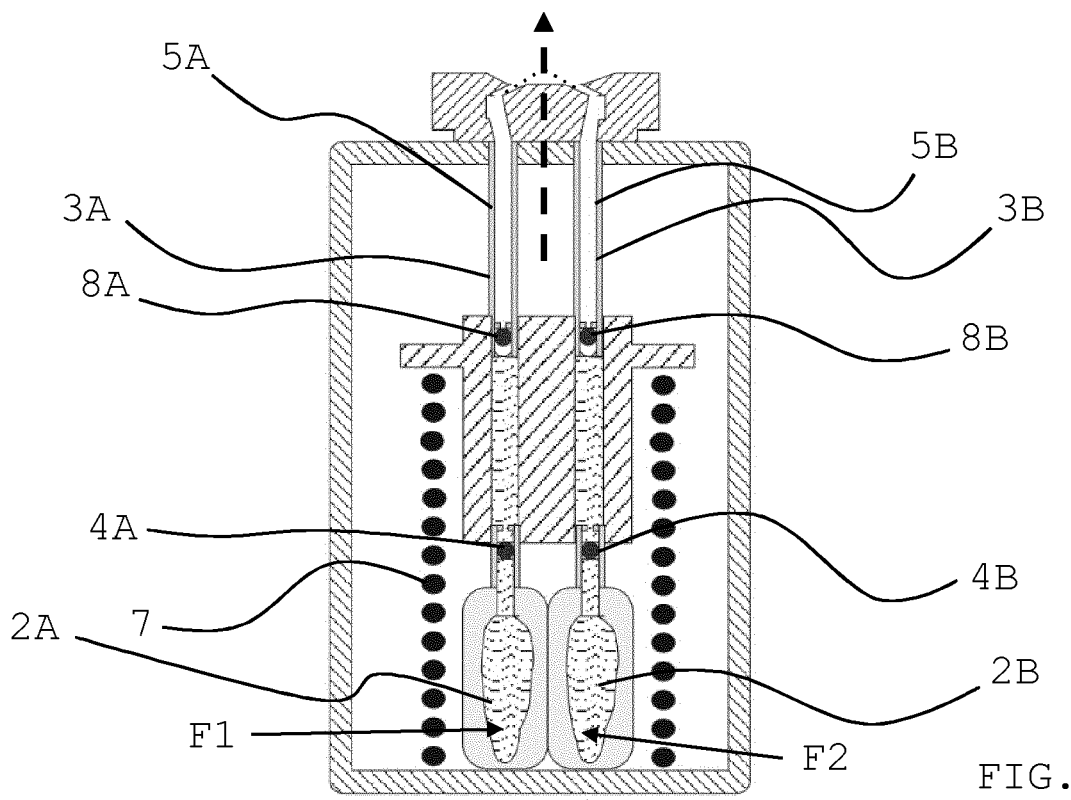
FIG. 3 shows the embodiment of FIG. 1 before initially filling the pumping chambers.
Figure 4:
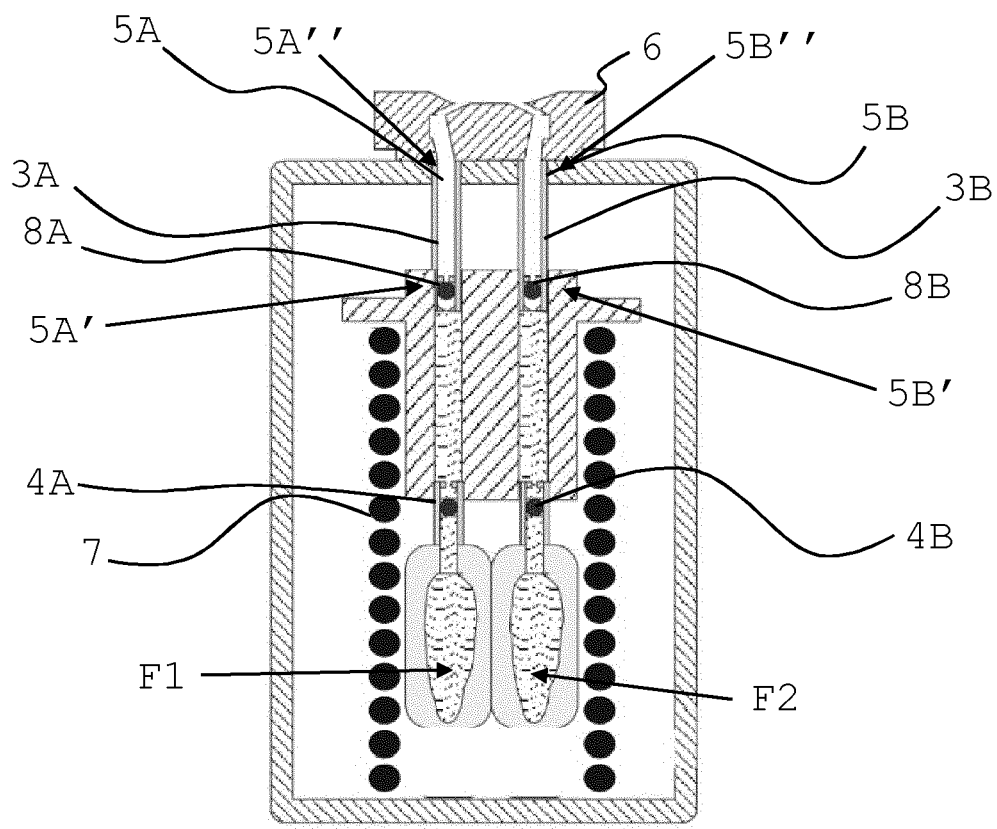
FIG. 4 shows the situation during the first activation.

In FIG. 4, the situation during the first activation of the inhalation device is shown. Means for the storage of potential energy 7 has been released from the loaded position as shown in FIG. 3. It pushes the pumping unit comprising pumping chamber 3A, 3B onto riser pipe 5A, 5B, the interior end 5A', 5B' of which coming closer to check valve 4A, 4B now being closed. As a result, the pressure inside pumping chamber 3A, 3B rises and keeps valve 4A, 4B being closed, but opens outlet valve 8A, 8B. Liquid F1, F2 rises inside riser pipe 5A, 5B towards its exterior end 5A", 5B" and nozzle 6.

Figure 5:
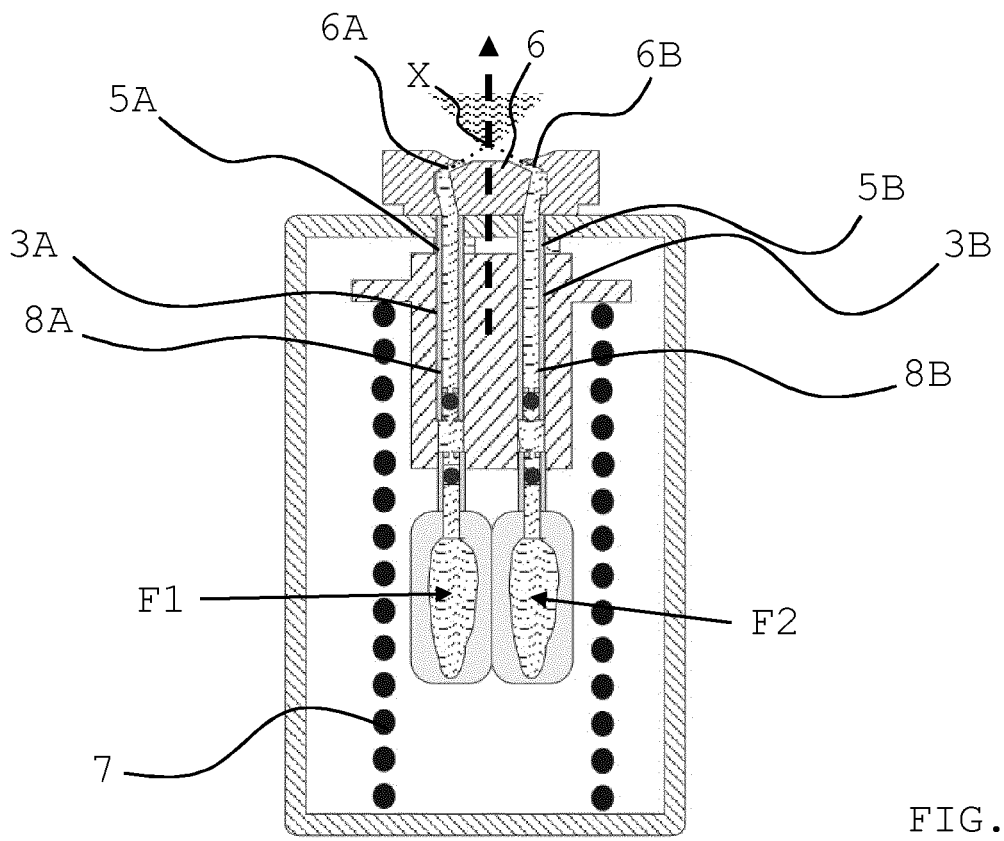
FIG. 5 shows the situation at the end of the first activation.

FIG. 5 shows the situation at the end of the first activation. Means for the storage of potential energy 7 is in its most relaxed end position (spring fully extended). Also, pumping chamber 3A, 3B has been pushed almost entirely onto according riser pipe 5A, 5B such that the respective interior volume of pumping chamber 3A, 3B reaches its minimum. Most of liquid F1, F2 previously contained inside pumping chamber 3A, 3B has passed outlet valve 8A, 8B into riser pipe 5A, 5B. Liquid F1, F2 already contained within riser pipe 5A, 5B has been pushed towards, and though, through ejection channels 6A and 6B of nozzle 6, where the desired nebulization takes place, producing a spray at common collision point X.

Figure 6:
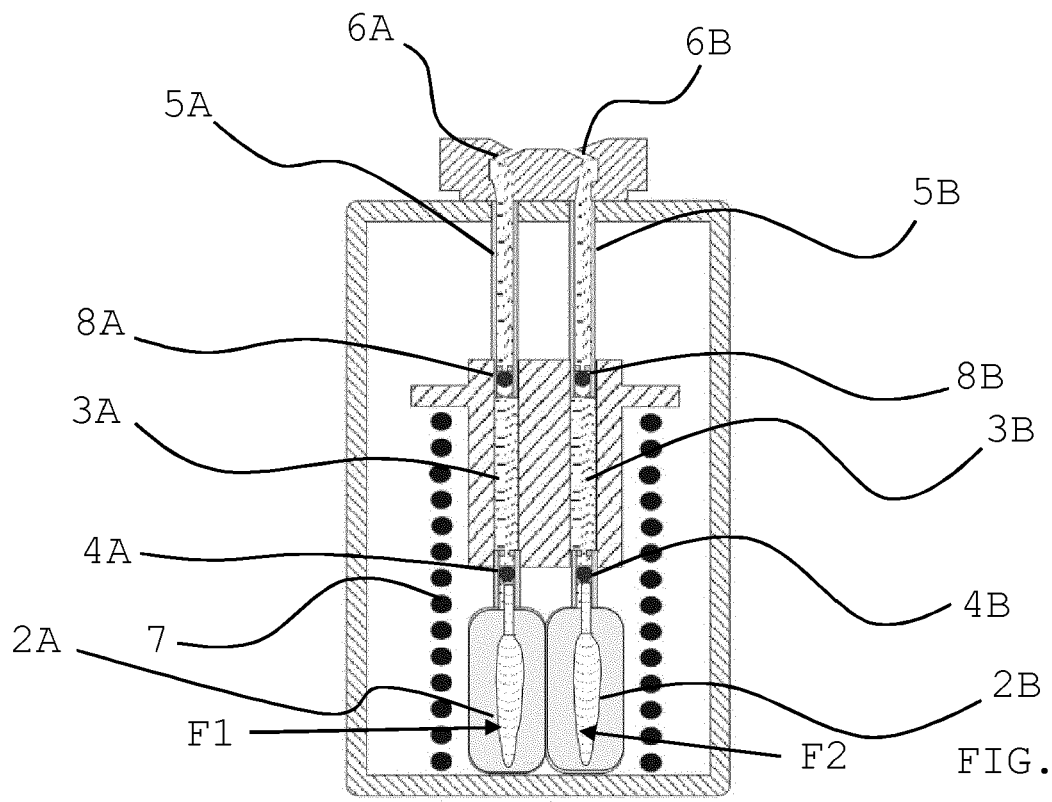
FIG. 6 shows the situation after re-filling the pumping chambers.
Figure 12:
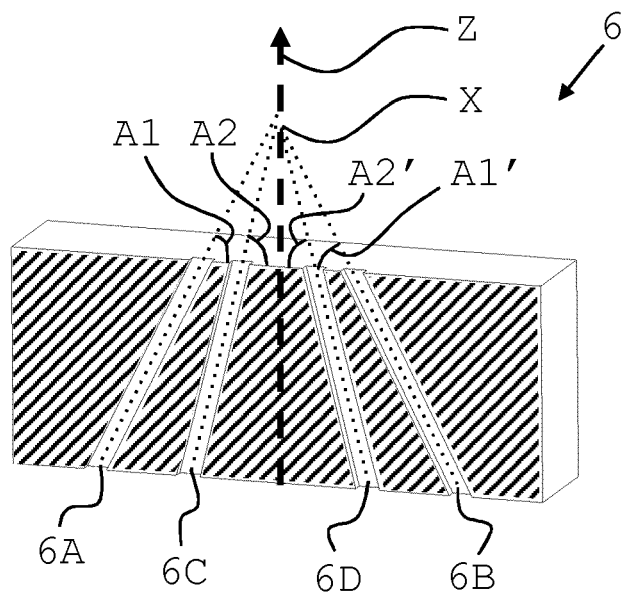
FIG. 12 shows a nozzle according to a fourth embodiment.
Figure 13:
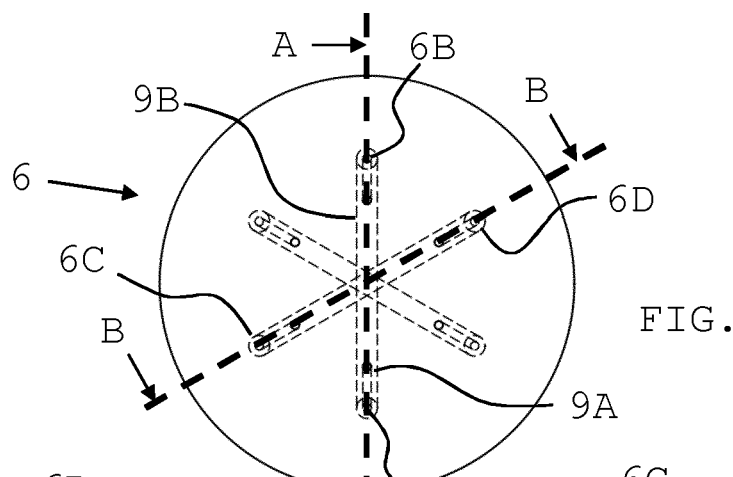
FIG. 13 shows a nozzle according to a fifth embodiment.

In FIG. 6, the situation after re-filling the pumping chamber 3A, 3B is depicted. Pumping chamber 3A, 3B has again been pulled off interior end 5A', 5B' of riser pipe 5A, 5B, increasing the respective interior volume of pumping chamber 3A, 3B. Means for the storage of potential energy 7 has been loaded (spring compressed). During movement of pumping chamber 3A, 3B away from riser pipe 5A, 5B, an underpressure develops in the interior volume, closing outlet valve 8A, 8B and opening check valve 4A, 4B. As a result, new liquid F1, F2 is drawn from reservoir 2A, 2B into pumping chamber 3A, 3B. The inhalation device's pumping chamber 3A, 3B is filled again and ready for the next ejection of liquid F1, F2 by releasing the spring.

In FIG. 7, a nozzle 6 comprising three ejection channels 6A, 6B, 6C is depicted. The ejection trajectories (dotted lines) intersect in one common collision point X. This collision point is located in plane P having a perpendicular orientation with respect to the main axis Z (this is the common orientation of the plane in which the collision point lies throughout this document, if not stated otherwise). All channels 6A, 6B, 6C are arranged symmetrically and three-dimensionally around main axis Z. The ejection angles (also plotted in FIG. 8 which is a detailed view of the nozzle tip; only angles A1, A2 are shown) as defined herein are identical. The line from which the intermediate angle I is measured is the main axis; thus, the intermediate angle is the collision angle. In this example, all individual trajectories are positioned on the surface of a truncated cone. Since the surface 6' of the truncated cone is parallel to the base circle (no reference numeral), in this example, the angles A1, A2 measured at both locations are identical. Preferably, the channels 6A, 6B, 6C are (laterally) closed with a closure such as a lid (not shown) or the like in a way that liquid (not shown) can pass through the channels, but cannot leave them in undesired (lateral) directions. This can e.g. be achieved in placing the truncated cone inside a cone shaped cap (not shown), the wall(s) of which form(s) a lid for the channels. The channels can be fabricated on the surface of the truncated cone as shown, but also as trenches in the surface of the cap.

Both types can be combined with each other, in that channels are provided alternating in cone and opening, or in that associated half-channels are provided in cone and opening.

In FIG. 9, a cross sectional view of a nozzle 6 is shown wherein, with respect to the nozzle's 6 main axis Z, again, all ejection angles A are identical (only one reference numeral A plotted); thus, all intermediate angles are the same as well, and they are all measured against the main axis Z. However, the ejection channels 6A-6D lie in a common cross sectional plane (hatching omitted), such that different collision points X1, X2 are provided. These are located in different planes P1, P2 perpendicular to the main axis Z, i.e. collision point X1 and X2 have different distances to the front surface 6' of nozzle 6. At the same time, all collision points X1, X2 are located on main axis Z. Ejection channels 6A and 6B form a first pair, and ejection channels 6C and 6D form a second pair. In this example, nozzle 6 is constructed as a "two-dimensional" block.

The present example can be used to produce a central stream (not shown) of an aerosol of a first liquid, and a surrounding sheath stream of an aerosol of a second liquid.

In FIG. 10, an embodiment is shown wherein the ejection channels 6A-6D are once again located on the surface of a truncated cone. In this setup, the ejection angles A1, A1' of a first pair of ejection channels 6A, 6B correspond to the ejection angles A2, A2' of a second pair of ejection channels 6C, 6D. However, due to ejection offsets the setup results in two different collision points X1 and X2. FIG. 11 is a detail of the tip of the nozzle. Note that angles A1, A2 in FIG. 10 are the same as in FIG. 11 since the base circle of the cone is parallel to the surface 6' of the truncated cone.

As can be seen in FIG. 10, for example, trajectory of channel 6B is slightly tilted away from the main axis Z in one direction, namely in direction of angle A1", whereas trajectory of channel 6D is tilted in the opposite direction, namely in direction of angle A2". Also, (presently similar) angles A1 and A2 are slightly smaller than angles A1* and A2* which start at the thin dashed lines. These represent lines that start at the base circle of the cone and end at its imaginary tip; channels along the thin dashed lines would have identical angles A1, A2 (and A1', A2', as well as A1", A2") as well, but also result in one common collision point. Therefore, in this example, two pairs of ejection channels 6A, 6B and 6C, 6D are provided, all having identical ejection angles A1, A2, A1' A2' (see FIG. 11), and thus, two collision points X1, X2 are provided, as in the previous example. A lateral ejection offset D exists which is the result of the aforesaid placement of angles. In this embodiment, along the nozzle's main axis Z, all collision points X1, X2 are located within the same plane (not shown) with respect to the nozzle's 6 front surface 6'. At the same time, all collision points X1, X2 a located laterally offset from main axis Z (lateral ejection offset D).

FIG. 12 depicts a nozzle 6 with four ejection channels 6A-6D whose ejection trajectories have pairwise different ejection angles (A1 and A1' are similar, as well as A2 and A2'), wherein the ejection channels (and the trajectories) lie in a common plane (hatched cross sectional plane). Nozzle 6 is again of the "two-dimensional" block-type. The angles A1, A1', A2, A2' are arranged in such a way that all ejection trajectories (dotted lines) intersect in one common collision point X.

In FIG. 13, a transparent top view on another embodiment of a nozzle is shown. For further details, reference is made to the description of FIGS. 12-15 below which relate to the same embodiment.

Figures 14, 15:
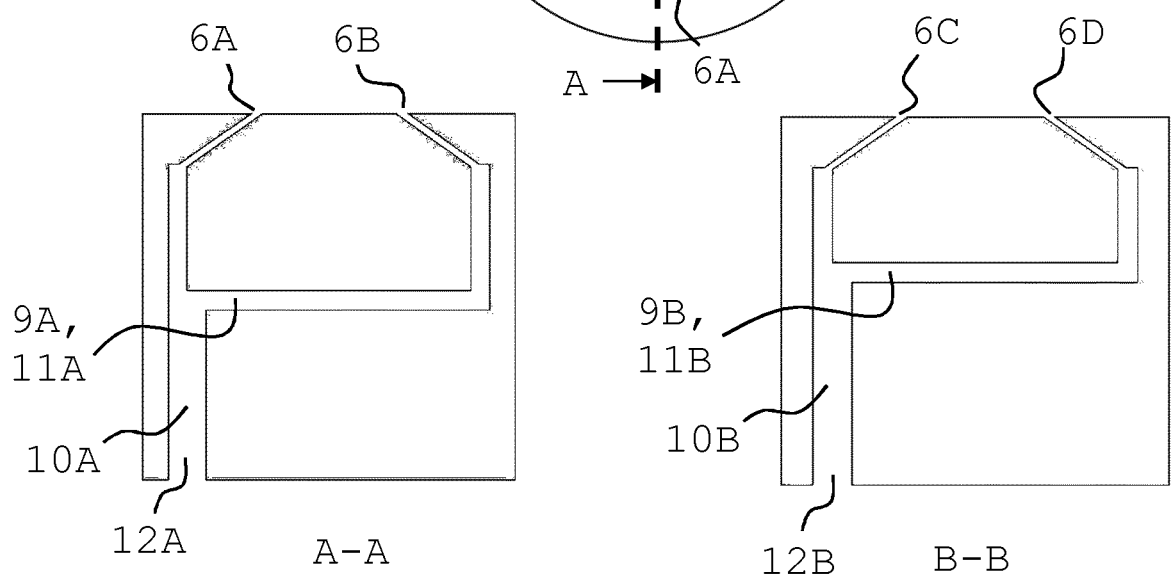
FIGS. 14-16 shows cross sections of a nozzle according to the fifth embodiment.

In FIGS. 14 and 15, two cross sections A-A and B-B of nozzle 6 from FIG. 11 are shown (hatching omitted) wherein the ejection channels 6A, 6B and 6C, 6D are connected to an upstream arranged common splitting chamber 9A, 9B. Thus, a separate chamber, or volume, is provided that is arranged between pumping chamber (not shown) and ejection channels 6A, 6B/6C, 6D, which has the purpose of splitting the liquid fed to the nozzle (optionally from several sources) before feeding it to the ejection channels 6A, 6B/6C, 6D.

In the depicted embodiment, two of the nozzle's 6 ejection channels 6A and 6B as well as 6C and 6D form a respective pair, and one main feed channel 10A, 10B is arranged to connect with the beginning of the first ejection channel 6A, 6C and a cross channel 11A, 11B exists that connects said main feed channel 10A, 10B with the end of the respective second ejection channel 6A, 6C. The cross channel 11A, 11B which serves as splitting chamber 9A, 9B runs perpendicular to main feed channel 10A, 10B. Only one respective inlet opening 12A, 12B exists which must be coupled to a pumping chamber or pumping unit (not shown).

In the depicted embodiment, the initially overlapping pairs of ejection channels, with respect to the main axis Z (not shown) which then also forms a symmetry axis, are in rotated positions relative to one another, e.g. by 60° (or another integer factor of 360°), and the respective cross channels 11A, 11B are, along said symmetry axis, spaced apart from one another, in order not to intersect with each other.

Figure 16:
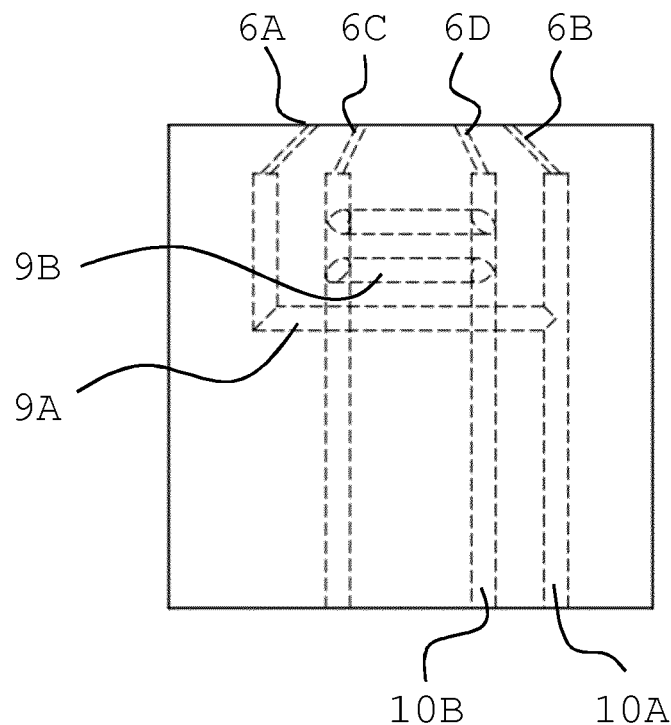

In FIG. 16 which is a transparent side view, a cross section containing hidden lines is depicted, such that all main axially spaced apart cross channels (third cross channel with reference numeral omitted) are well visible. Only two pairs of ejection channels can be seen because of the view direction.

Figure 17:
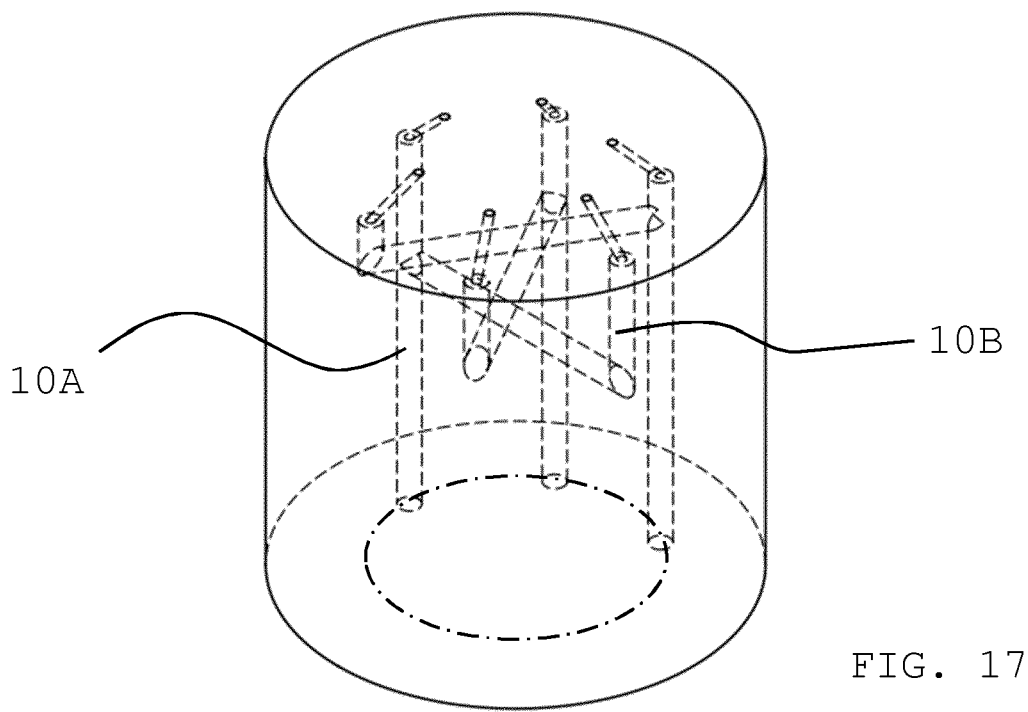
FIG. 17 shows a three-dimensional view of this embodiment.

The aforementioned design can also be seen in FIG. 17 which is a three-dimensional transparent view of nozzle 6 containing the cross sections of FIGS. 14 and 15. By virtually rotating the cross sections, a compact and simple nozzle is obtained whose inlet openings (reference numerals omitted) are located on a circular path (dash-dotted circle). Thus, the respective interface to the upstream arranged component (i.e. pumping chamber, valve section, not depicted) can be designed to be relatively simple.

LIST OF REFERENCES 1 housing
2,2A,2B reservoir
3,3A,3B pumping chamber
4,4A,4B check valve
5,5A,5B riser pipe
5A',5B' interior end
5A",5B" exterior end
6 nozzle
6' front surface
6A-6D ejection channels
7 means for the storage of potential energy
8,8A,8B outlet valve
9A,9B splitting chamber
10,10A,10B main feed channel
11,11A,11B cross channel
12,12A,12B inlet opening
F,F1,F2 liquid
X,X1,X2 collision point
A,A1,A2 ejection angle
A1*,A2*,A1',A2',A1",A2" angle
I intermediate angle
Z main axis
D ejection offset

The invention claimed is:

1. An inhalation device for the generation of an aerosol, the device comprising at least one reservoir containing a liquid composition comprising pirfenidone, wherein the inhalation device is a pump-actuated inhaler adapted to release upon actuation a metered dose of the liquid composition from the reservoir, wherein the inhalation device comprises a housing, inside this housing at least one reservoir for storing said liquid composition, at least one pumping unit with at least one pumping chamber for generation of a pressure inside said pumping chamber, wherein the pumping chamber is fluidically connected with the reservoir via a check valve which blocks in direction of the reservoir, at least one riser pipe which can be received with at least one reservoir-facing, interior end in said pumping chamber, and a nozzle which is connected liquid-tight to an exterior end of the riser pipe, wherein the interior volume of the at least one pumping chamber is changeable by means of relative motion along a longitudinal axis of the pumping chamber to the riser pipe, and wherein the at least one riser pipe is immobile and firmly attached to the housing or to the nozzle, and the at least one pumping chamber is moveable relative to the housing or to the nozzle, wherein the nozzle has a main axis and at least three ejection channels adapted to eject liquid along respective ejection trajectories, wherein at least one collision point is provided at which at least two of said ejection trajectories intersect with one another.

2. The inhalation device of claim 1, wherein the metered dose of the liquid composition released upon actuation has a volume of at least 20 μl.

3. The inhalation device of claim 1, wherein a single dose of the liquid composition comprising pirfenidone is released by one actuation or a plurality of actuations of the inhalation device.

4. The inhalation device of claim 3, wherein a single dose of the liquid composition comprising pirfenidone comprises an amount of at least 5.0 mg of pirfenidone.

5. The inhalation device of claim 1, comprising four ejection channels adapted to eject the composition along respective ejection trajectories, wherein two collision points are provided, and wherein at each of the two collision points two of said ejection trajectories intersect with one another.

6. The inhalation device of claim 1, wherein all ejection angles at which the individual trajectories leave the nozzle are identical, or wherein at least one of said ejection angles differs from the other ejection angles.

7. The inhalation device of claim 1, wherein at least two, or all collision points are located within the same plane perpendicular to the main axis of the nozzle, or wherein at least two, or all collision points are located on different planes perpendicular to the main axis of the nozzle.

8. The inhalation device of claim 1, wherein with respect to the nozzle's main axis, all collision points are located on the main axis, or wherein with respect to the nozzle's main axis, at least one collision point is offset from the main axis.

9. The inhalation device of claim 1, wherein all of the nozzle's ejection channels have the same cross section, or wherein at least one of the nozzle's ejection channels has a different cross section from that of another ejection channel.

10. The inhalation device according to claim 1, wherein at least two ejection channels of the nozzle share a common inlet and have intersecting trajectories such as to form a pair or group of ejection channels, or wherein all ejection channels of the nozzle have distinct inlets.

11. The inhalation device of claim 1, wherein two ejection channels form a pair, the device further comprising a main feed channel arranged to connect to an upstream end of the first ejection channel, and a cross channel that connects said main feed channel with the upstream end of the second ejection channel.

12. The inhalation device according to claim 1, with a nozzle having a plurality of pairs, wherein the exit openings of the ejection channels of one of the pairs, with respect to the main axis which forms a symmetry axis, are in rotated positions relative to the exit openings of the ejection channels of another one of the pairs, and wherein the respective cross channels are, along said symmetry axis, spaced apart from one another.

13. The inhalation device according to claim 11, wherein the nozzle exhibits a front side and a back side opposite to the front side, wherein the front side comprises the exit openings of the ejection channels, and wherein the back side is essentially flat and comprises a plurality of openings that form inlets to said main feed channel(s).

14. The inhalation device of claim 1, wherein the nozzle is constructed as a stack of two-dimensional plates.

15. The inhalation device of claim 1, wherein the nozzle is constructed from a three-dimensional rotation symmetric basic shape.

16. The inhalation device of claim 1, wherein the reservoir is firmly attached to the pumping chamber and thus moveable inside the housing; or wherein the reservoir is connected to the pumping chamber by means of a flexible element, and firmly attached to the housing.

17. A reservoir containing a liquid composition comprising pirfenidone, wherein the reservoir is adapted for use with an inhalation device according to claim 1.

18. The reservoir of claim 17, wherein the liquid composition comprising pirfenidone is an aqueous solution or suspension, optionally comprising one or more excipients, such as one or more buffering agents and/or co-solvents.

19. A method for delivering pirfenidone to a subject in need thereof, comprising the step of providing an inhalation device according to claim 1 to said subject.

20. A method of treating a subject suffering from a lung disease or condition, the method comprising a step of administering pirfenidone to said subject using a device according to claim 1.

21. The method of claim 20, wherein the lung disease or condition is an interstitial lung disease.

22. The method of claim 20, wherein the lung disease or condition is selected from pulmonary fibrosis and idiopathic pulmonary fibrosis (IPF).

23. The inhalation device of claim 1, wherein the liquid composition comprising pirfenidone is an aqueous solution or suspension, optionally comprising one or more excipients, such as one or more buffering agents and/or co-solvents.

* * * * *

UNITED STATES PATENT AND TRADEMARK OFFICE
CERTIFICATE OF CORRECTION

| | | |
|---|---|---|
| PATENT NO. | : 12,048,801 B2 | Page 1 of 1 |
| APPLICATION NO. | : 16/624224 | |
| DATED | : July 30, 2024 | |
| INVENTOR(S) | : Bartels et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1004 days.

Signed and Sealed this
Eighteenth Day of March, 2025

Coke Morgan Stewart
*Acting Director of the United States Patent and Trademark Office*